United States Patent
Spilling et al.

(10) Patent No.: US 10,047,112 B2
(45) Date of Patent: Aug. 14, 2018

(54) FLUORESCENT LABELED INHIBITORS

(71) Applicant: The Curators of the University of Missouri, St. Louis, MO (US)

(72) Inventors: Christopher D. Spilling, St. Louis, MO (US); Benjamin P. Martin, St. Louis, MO (US); Stephane Canaan, Paris (FR); Jean-Francois Cavalier, Paris (FR)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/120,255

(22) PCT Filed: Feb. 23, 2015

(86) PCT No.: PCT/US2015/017137
§ 371 (c)(1),
(2) Date: Aug. 19, 2016

(87) PCT Pub. No.: WO2015/127381
PCT Pub. Date: Aug. 27, 2015

(65) Prior Publication Data
US 2017/0066790 A1 Mar. 9, 2017

Related U.S. Application Data

(60) Provisional application No. 61/966,363, filed on Feb. 21, 2014.

(51) Int. Cl.
| | | |
|---|---|---|
| *C07F 9/6574* | (2006.01) | |
| *C07F 9/6571* | (2006.01) | |
| *G01N 33/58* | (2006.01) | |
| *A01N 57/36* | (2006.01) | |
| *G01N 33/573* | (2006.01) | |

(52) U.S. Cl.
CPC ......... *C07F 9/65742* (2013.01); *A01N 57/36* (2013.01); *C07F 9/65744* (2013.01); *C07F 9/657163* (2013.01); *C07F 9/657181* (2013.01); *G01N 33/573* (2013.01); *G01N 33/582* (2013.01); *C07B 2200/05* (2013.01); *G01N 2333/35* (2013.01); *G01N 2333/916* (2013.01); *G01N 2333/92* (2013.01)

(58) Field of Classification Search
CPC .......................... C07F 9/65742; A01N 57/36
See application file for complete search history.

(56) References Cited

U.S. PATENT DOCUMENTS 6,756,402 B2   6/2004   Vertesy et al.
7,772,402 B2   8/2010   Hermetter et al.

FOREIGN PATENT DOCUMENTS

| WO | 2008/025449 A1 | 3/2008 |
|---|---|---|
| WO | 2013/007570 A1 | 1/2013 |
| WO | 2015/127381 | 8/2015 |

OTHER PUBLICATIONS

Bandyopadhyay et al., "Synthesis and Biological Evaluation of a Phosphate Analog of the Natural Acetyl Cholinesterase Inhibitor Cyclophostin", The Journal of Organic Chemistry, 2008, pp. 8386-8391, vol. 73.
Brodin et al., "High-Content Screening in Infectious Diseases", Current Opinion in Chemical Biology, 2011, pp. 534-539, vol. 15.
Brust et al., "Mycobacterium Tuberculosis Lipolytic Enzymes as Potential Biomarkers for the Diagnosis of Active Tuberculosis", PLOS One, Sep. 2011, pp. 1-10, vol. 6, Issue 9, e25078.
Christophe et al., "High Content Screening Identifies Decaprenyl-Phosphoribose 2' Epimerase as a Target for Intracellular Antimycobacterial Inhibitors", PLOS Pathogens, Oct. 2009, pp. 1-10, vol. 5, Issue 10, e1000645.
Delorme et al., "MmPPOX Inhibits Mycobacterium Tuberculosis Lipolytic Enzymes Belonging to the Hormone-Sensitive Lipase Family and Alters Mycobacterial Growth", PLOS ONE, Sep. 2012, pp. 1-9, vol. 7, Issue 9, e46493.
Delorme et al., "Supported Inhibitor for Fishing Lipases in Complex Biological Media and Mass Spectrometry Identification", Biochimie, 2014, pp. 124-134, vol. 107.
Dutta et al., "Sythesis and Kinetic Analysis of Some Phosphonate Analogs of Cyclophostin as Inhibitors of Human Acetylcholinesterase", Bioorganic & Medicinal Chemistry, 2010, pp. 2265-2274, vol. 18.
Flipo et al., "Ethionamide Boosers: Synthesis, Biological Activity, and Structure—Activity Relationships of a Series of 1,2,4-Oxadiazole EthR Inhibitors", Journal of Medicinal Chemistry, 2011, pp. 2994-3010, vol. 54.
Grzegorzewicz et al., "Inhibition of Mycolic Acid Transport Across the Mycobacterium Tuberculosis Plasma Membrane", Nature Chemical Biology, Apr. 2012, pp. 334-341, vol. 8.
Han et al., "G-(Monophenyl)phosphono Glutamate Analogues as Mechanism-Based Inhibitors of g-glutamyl Transpeptidase", Bioorganic & Medicinal Chemistry, 2006, pp. 6043-6054, vol. 14.
Hendrickson, "Fluorescence-Based Assays of Lipases Phospholipases, and Other Lipolytic Enzymes", Analytical Biochemistry, 1994, pp. 1-8, vol. 219, Academic Press, Inc.
International Search Report and Written Opinion for PCT/US2015/017137 dated May 29, 2015.
Joossens et al., "Development of Irreversible Diphenyl Phosphonate Inhibitors for Urokinase Plasminogen Activator", Journal of Medicinal Chemistry, 2004, pp. 2411-2413, vol. 47.
Kremer et al., "Identification and Structural Characterization of an Unusual Mycobacterial Monomeromycolyl-diacylglycerol", Molecular Microbiology, 2005, pp. 1113-1126, vol. 57, No. 4.
Kurokawa et al., "Cyclophostin, Acetylcholinesterase Inhibitor From Streptomyce Lavendulae", The Journal of Antibiotics, Aug. 1993, vol. 46, No. 8.
Liu et al., "Activity-Based Protein Profiling: The Serine Hydrolases", Proceedings of the National Academy of Sciences, Dec. 21, 1989, pp. 14694-14699, vol. 96, No. 26.

(Continued)

*Primary Examiner* — Golam M Shameem
(74) *Attorney, Agent, or Firm* — Thompson Coburn LLP; William A. Holtz

(57) ABSTRACT

Provided herein are a series of fluorescently labeled phosphonate and phosphate compounds such as can be used for affinity probes to detect certain enzymes including lipases. Also provided are methods of making and using such compounds.

20 Claims, 14 Drawing Sheets

(56) References Cited

OTHER PUBLICATIONS

Malla et al., "The First Total Synthesis of (±)-Cyclophostin and (±)-Cyclipostin P: Inhibitors of the Serine Hydrolases Acetyl Cholinesterase and Hormone Sensitive Lipase", Organic Letters, 2011, pp. 3094-3097, vol. 13, No. 12.
Oleksyszyn et al., "Irreversible Inhibition of Serine Proteases by Peptide Derivatives of (a-Aminoalkyl) phosphonate Diphenyl Esters", Biochemistry, 1991, pp. 485-493, vol. 30.
Point et al., "Enantioselective Inhibition of Microbial Lipolytic Enzymes by Nonracemic Monocyclic Enolphosphonate Analogues of Cyclophostin", Journal of Medicinal Chemistry, 2013, pp. 4393-4401, vol. 56.
Point et al., "Synthesis and Kinetic Evaluation of Cyclophostin and Cyclipostins Phosphonate Analogs as Selective and Potent Inhibitors of Microbial Lipases", Journal of Medicinal Chemistry, 2012, pp. 10204-10219, vol. 55.
Raghavan et al., "Chemical Probes for Profiling Fatty Acid-Associated Proteins in Living Cells", Bioorganic & Medicinal Chemistry Letters, 2008, pp. 5982-5986, vol. 18.
Ransac, "Covalent Inactivation of Lipases", Methods in Enzymology, 1997, pp. 190-231, vol. 286.
Rawat et al., "Antituberculosis Drug Research: A Critical Overview", Medicinal Research Reviews, Jul. 2013, pp. 1-12.
Romanenko et al., "Fluorinated Phosphonates: Synthesis and Biomedical Application", Chemical Reviews, 2006, pp. 3868-3935, vol. 106.
Roy et al., "Synthesis of the C(18)-C(34) Fragment of Amphidinolide C and the C(18)-C(29) Fragment of Amphidinolide F", Organic Letters, 2010, pp. 5326-5329, vol. 12, No. 22.
Schmidinger et al., "Novel Fluorescent Phosphonic Acid Esters for Discrimination of Lipases and Esterases", ChemBioChem, 2005, pp. 1776-1781, vol. 6.
Schulze et al., "Salinipostins A-K, Long-Chain Bicyclic Phosphotriesters as a Potent and Selective Antimalarial Chemotype", The Journal of Organic Chemistry, 2015, pp. 1312-1320, vol. 80.
Segall et al., "Cannabinoid CB1 Receptor Chemical Affinity Probes: Methods Suitable for Preparation of Isopropyl [11,12-3H]Dodecylfluorophosphonate and [11,12-3H]Dodecanesulfonyl Fluoride", Synthetic Communications, 2003, pp. 2151-2159, vol. 33, No. 12.
Sieñczyk et al., "New Potent Cathepsin G Phosphonate Inhibitors", Bioorganic & Medicinal Chemistry, 2008, pp. 8863-8867, vol. 16.
Stanley et al., "Indentification of Novel Inhibitors of M. Tuberculosis Growth Using Whole Cell Based High-Throughput Screening", American Chemical Society Chemical Biology, 2012, pp. 1377-1384, vol. 7.
Susani-Etzerodt et al., "A Versatile Library of Activity-Based Probes for Fluorescence Detection and/or Affinity Isolation of Lipolytic Enzymes", Chemistry and Physics of Lipids, 2006, pp. 60-68, vol. 144.
Vasilieva et al., "Rat Hormone Sensitive Lipase Inhibition by Cyclipostins and Their Analogs", Bioorganic & Medicinal Chemistry, 2015, pp. 944-952, vol. 23.
Vértesy et al., "Cyclipostins, Novel Hormone-Sensitive Lipase Inhibitors from *Streptomyces* sp. DSM 13381: II. Isolation, Structure Elucidation and Biological Properties", The Journal of Antibiotics, May 2002, pp. 480-494, vol. 55, No. 5.
Walker, "The Dansyl Method for Identifying N-Terminal Amino Acids", In Basic Protein and Peptide Protocols, 1994, pp. 321-328, vol. 32.
Walker, "The Dansyl-Edman Method for Peptide Sequencing", In Basic Protein and Peptide Protocols, 1994, pp. 329-334, vol. 32.
West et al., "Inhibitors of an Essential Mycobacterial Cell Wall Lipase (Rv3802c) as Tuberculosis Drug Leads†", Chemical Communications, 2011, pp. 5166-5168, vol. 47.
Wink et al., "Cyclipostins: Novel Hormone-Sensitive Lipase Inhibitors from *Streptomyces* sp. DSM 13381: I. Taxonomic Studies of the Porducer Microorganism and Fermentation Results", The Journal of Antibiotics, May 2002, pp. 472-479, vol. 55, No. 5.
Zumla et al., "Advances inthe Development of New Tuberculosis Drugs and Treatment Regimens", Nature, May 2013, pp. 388-404, vol. 12.

1j, $R^2$ = Et, $R^1$ = 
Cyclipostin S

1k, $R^2$ = Pr, $R^1$ = 
Cyclipostin T

1l, $R^2$ = Pr, $R^1$ = 
Cyclipostin T2

Scheme 2

FLUORESCENT LABELED INHIBITORS

CROSS REFERENCE TO RELATED APPLICATIONS

This application is a 35 U.S.C. § 371 National Phase Application of International Patent Application No. PCT/US2015/017137, filed Feb. 23, 2015, and incorporated herein by reference in its entirety, which claims the benefit of U.S. Provisional Application No. 61/966,363 filed Feb. 21, 2014 which is hereby incorporated herein by reference in its entirety.

FIELD OF THE INVENTION

The present invention relates to affinity probes and in some aspects more specifically to a series of fluorescently labeled phosphonate- and phosphate-based enzyme inhibitors including lipase inhibitors and methods of their production and application in sensing and detecting enzymes from organisms such as bacteria.

BACKGROUND

*Mycobacterium tuberculosis* (*M. tb*) is a global public health challenge. In 2012, the World Health Organization (WHO) reported 8.6 million new cases and 1.3 million deaths caused by *M. tb*. Tuberculosis (TB) is the most deadly infectious disease worldwide and remains a challenge, especially in sub Saharan Africa, Russia and Eastern Europe. The emergence of multiple drug resistant (MDR) and extensively drug resistant (XDR) strains with the high number of HIV cases highlight the pressing need for novel therapeutic approaches.[2a]

In 2013, Zumla et al. reported that "no new TB drug classes have been developed or approved for drug susceptible TB since the current 6-month four-drug combination was introduced in the 1970s."[2c] However, it was also stated that "significant effort is being invested in drug development for drug susceptible TB" and that "there is growing awareness of the need for drugs that can kill *M. tuberculosis* in its different physiological states."[2c] Many of the promising new molecules in development are either repurposed drug compounds or new derivatives of known anti-mycobacterial drugs.[2c-e] Moreover, many of these (new) drugs specifically target the cell wall biosynthesis, but none are reported to target intracellular lipid metabolism.

Primo-infection with *M. tb* leads to the formation of granulomas in the lung, where some of the infected macrophages accumulate lipids in lipid bodies (LB) giving the cells a foamy appearance.[3] In such foamy macrophages (FM), bacilli accumulate lipids and can persist in a non-replicating state for decades, but can also be reactivated to cause acute disease.[4] A better understanding of how bacilli persist inside lipid-rich FM is needed to find new ways to fight the disease. To persist inside the FM, *M. tb* hydrolyzes host lipids into fatty acids that are reused as lipid reserves within intracytoplasmic lipid inclusions (ILI). Recent results suggest a direct link between the presence of ILI in mycobacteria and their inability to divide. The latter may be of central importance for mycobacterial persistence within granulomas. Over the past ten years, lipolytic enzymes, which are responsible for the release of long-chain fatty acids, have become a focus of research.[5a] These enzymes, strongly involved in the host-pathogen cross-talk, play several roles in the physiopathology of the disease during both the active and persistent phases of infection. Although their role in the control of host lipid breakdown and ILI consumption during infection is documented, the molecular mechanisms involved in these processes remain elusive. Recently, these enzymes have become mycobacterial drug targets (Canaan and others).[5b-d] Accordingly, finding ways to inhibit their activity could pave the way for discovery of new modalities for the treatment of TB as well as potentially other uses.

Phosphorus fluorides [RP(O)F(OR)] such as DIFP [(iPrO)2P(O)F] have become important tools in investigating serine hydrolase biochemistry. However, they are very reactive which makes them unstable in aqueous solution and somewhat promiscuous in their interaction with enzymes. None-the-less, several very useful affinity probes based on phosphorus fluorides have been developed.[18] Phenyl phosphonate esters [RP(O)(OPh)2] are another example of irreversible hydrolase inhibitor.[19] They are somewhat less reactive than the fluorides, although the reactivity can be tuned by substituents on the phenyl leaving group (e.g., $NO_2$). Due to the relatively simple structure of such inhibitors [R—P(O)X(OR), X=F or OAr] structural modifications for SAR can be somewhat limited. Other *M. tb* lipase inhibitors are derivatives of the β-lactone anti-obesity drug Orlistat. They are, in some cases potent, but can be less non-specific.

SUMMARY

Provided herein are compounds and the design, synthesis, and use of such compounds that specifically inhibit the activity of enzymes.

One aspect is directed to a compound comprising a cyclic enolphosphonate or a cyclic enolphosphate attached to a fluorescent label.

In certain embodiments, the compound has the structure:

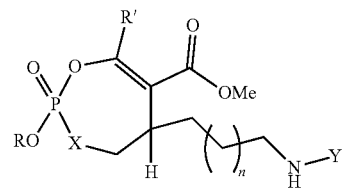

wherein n is any of 1 to 20; wherein R is alkyl, benzyl, or aryl; wherein R' is any of C1 to C20; wherein X is O or $CH_2$; and wherein Y is a fluorescent label. In certain embodiments, R' is a methyl group. In certain specific embodiments, n is 7. In certain specific embodiments, X is O. In certain specific embodiments, X is $CH_2$. In certain embodiments, the compound has the structure:

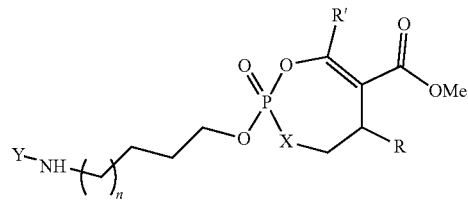

wherein n is any of 1 to 20; wherein R is alkyl, benzyl, or aryl; wherein R' is any of C1 to C20; wherein X is O or $CH_2$; and wherein Y is a fluorescent label. In certain embodiments, R' is a methyl group. In certain specific embodiments, n is 9. In certain specific embodiments, X is O. In certain specific embodiments, X is CH$_2$.

In certain embodiments of a compound disclosed herein, the fluorescent label is nitrobenzo-2-oxa-1,3-diazole (NBD) or the fluorescent label is a dansyl group.

In certain embodiments, the compound has the structure:

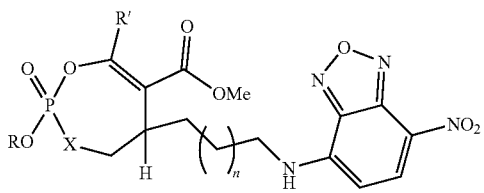

wherein n is any of 1 to 20; wherein R is alkyl, benzyl, or aryl; wherein R' is any one of C1 to C20; and wherein X is O or CH$_2$. In certain embodiments, the compound has the structure:

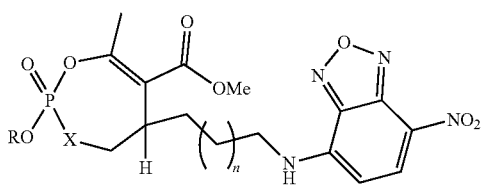

wherein n is any of 1 to 20; wherein R is alkyl, benzyl, or aryl; and wherein X is O or CH$_2$. In certain embodiments, the compound has the structure:

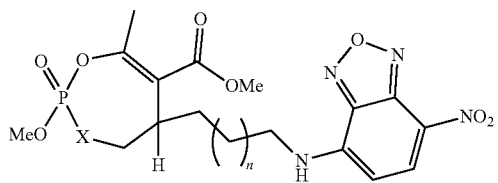

wherein n is any of 1 to 20 and wherein X is O or CH$_2$. In certain specific embodiments of a compound disclosed herein, n is 7. Thus, in certain embodiments, the compound has the structure:

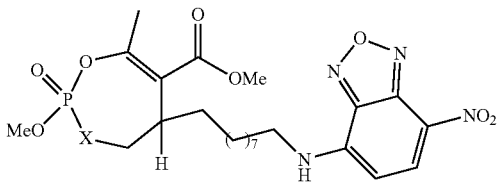

wherein X is O or CH$_2$. In certain specific embodiments of a compound disclosed herein, X is O and in certain other specific embodiments of a compound disclosed herein, X is CH$_2$.

In certain embodiments, the compound has the structure:

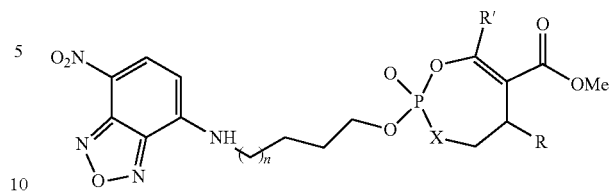

wherein n is any of 1 to 20; wherein R is alkyl, benzyl, or aryl; wherein R' is C1 to C20; and wherein X is O or CH$_2$. In certain embodiments, the compound has the structure:

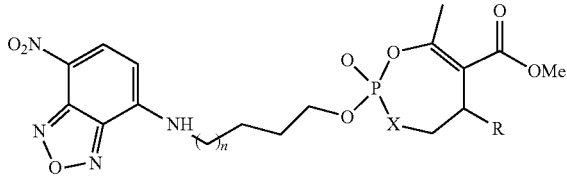

wherein n is any of 1 to 20; wherein R is alkyl, benzyl, or aryl; and wherein X is O or CH$_2$. In certain embodiments, the compound has the structure:

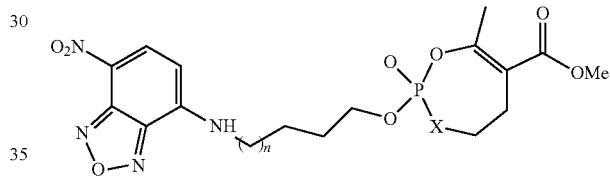

wherein n is any of 1 to 20 and wherein X is O or CH$_2$. In certain specific embodiments of a compound disclosed herein, n is 9. Thus, in certain embodiments, the compound has the structure:

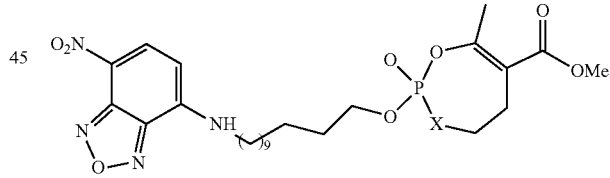

wherein X is O or CH$_2$. In certain specific embodiments of a compound disclosed herein, X is O and in certain other specific embodiments of a compound disclosed herein, X is CH$_2$.

In certain embodiments, the compound has the structure:

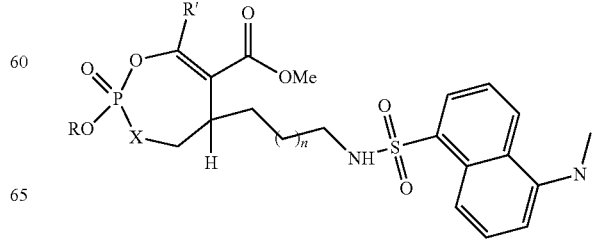

wherein n is any of 1 to 20; wherein R is alkyl, benzyl, or aryl; R' is C1 to C20; and wherein X is O or CH$_2$. In certain embodiments, the compound has the structure:

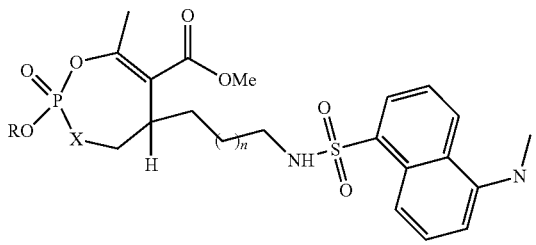

wherein n is any of 1 to 20; wherein R is alkyl, benzyl, or aryl; and wherein X is O or CH$_2$. In certain embodiments, the compound has the structure:

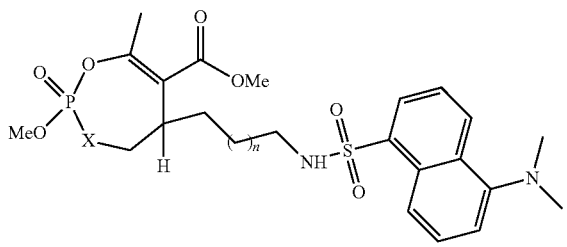

wherein n is any of 1 to 20 and wherein X is O or CH$_2$. In certain specific embodiments of a compound disclosed herein, n is 7. Thus, in certain embodiments, the compound has the structure:

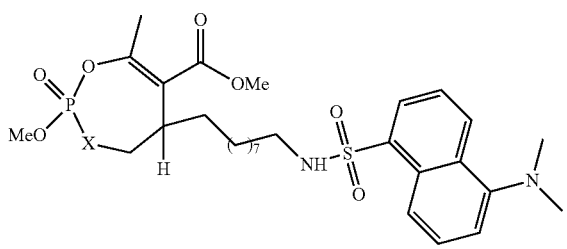

wherein X is O or CH$_2$. In certain specific embodiments of a compound disclosed herein, X is O and in certain other specific embodiments of a compound disclosed herein, X is CH$_2$.

In certain embodiments, the compound has the structure:

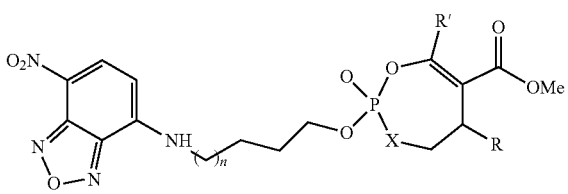

wherein n is any of 1 to 20; wherein R is alkyl, benzyl, or aryl; R' is C1 to C20; and wherein X is O or CH$_2$. In certain embodiments, the compound has the structure:

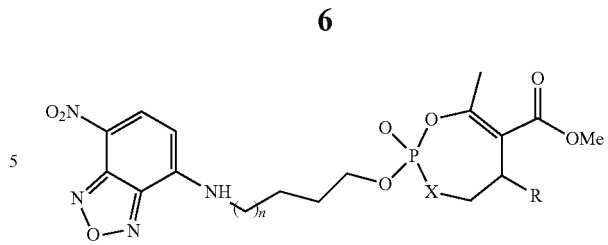

wherein n is any of 1 to 20; wherein R is alkyl, benzyl, or aryl; and wherein X is O or CH$_2$. In certain embodiments, the compound has the structure:

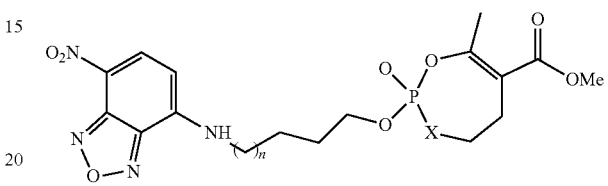

wherein n is any of 1 to 20 and wherein X is O or CH$_2$. In certain specific embodiments of a compound disclosed herein, n is 9. Thus, in certain embodiments, the compound has the structure:

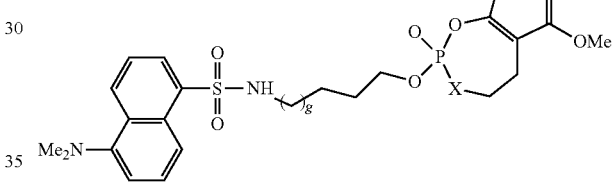

wherein X is O or CH$_2$. In certain specific embodiments of a compound disclosed herein, X is O and in certain other specific embodiments of a compound disclosed herein, X is CH$_2$.

In certain embodiments, a compound disclosed herein inhibits a lipase. In certain embodiments, the lipase is a mycobacterial lipase.

In certain embodiments, a compound disclosed herein covalently binds to an active site serine residue of an enzyme. In certain embodiments, the enzyme is a lipase. In certain embodiments, the enzyme is a mycobacterial lipase.

Another aspect of the invention provides for methods of inhibiting an enzyme. In certain embodiments, the method comprises contacting the enzyme with a compound disclosed herein. In certain specific embodiments, the enzyme comprises an active site serine residue. In certain specific embodiments, the enzyme is a lipase. In certain specific embodiments, the enzyme is a mycobacterial lipase.

Another aspect of the invention provides for detecting an enzyme. In certain embodiments, the method comprises contacting the enzyme with a compound disclosed herein to covalently link the compound to the enzyme and visualizing the fluorescent label of the compound. In certain embodiments, the enzyme comprises an active site serine residue. In certain embodiments, the enzyme is a lipase. In certain embodiments, the enzyme is a mycobacterial lipase.

BRIEF DESCRIPTION OF THE DRAWINGS/FIGURES

FIG. 4 shows synthesis Scheme 1 of the disclosure.

FIG. 5 shows synthesis Scheme 2 of the disclosure.

FIG. 6 shows synthesis Scheme 3 of the disclosure.

FIG. 7 shows synthesis Scheme 4 of the disclosure.

FIG. 8 shows synthesis Scheme 5 of the disclosure.

FIG. 9 shows synthesis Scheme 6 of the disclosure.

FIG. 10 shows synthesis Scheme 7 of the disclosure.

FIG. 11 shows synthesis Scheme 8 of the disclosure.

FIG. 12 shows a mechanism of affinity probe attachment to an enzyme with an active site serine residue.

FIG. 13 shows labelling of LipY with a fluorescently labelled probe.

DETAILED DESCRIPTION

To the extent necessary to provide descriptive support, the subject matter and/or text of the appended claims is incorporated herein by reference in their entirety. It will be understood by all readers of this written description that the exemplary embodiments described and claimed herein may be suitably practiced in the absence of any recited feature, element or step that is, or is not, specifically disclosed herein.

Throughout this disclosure, the term "a" or "an" entity refers to one or more of that entity; for example, "a compound," is understood to represent one or more compounds. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to whom this disclosure is directed. Numeric ranges are inclusive of the numbers defining the range.

All methods described herein can be performed in any suitable order unless otherwise indicated herein.

No language or terminology in this specification should be construed as indicating any non-claimed element as essential or critical.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value is intended to be included therein, and all smaller subranges are also included.

The headings provided herein are not limitations of the various aspects of the disclosure, which can be had by reference to the specification as a whole.

The present disclosure provides for compounds and the design and synthesis of compounds that specifically inhibit the activity of enzymes. In certain embodiments, the enzyme is a hydrolase. In certain embodiments, the enzymes contain a serine residue in the enzyme active site (e.g., serine lipases), referred to herein as an "active site serine" residue. In certain specific embodiments, the enzyme is a lipase, such as a microbial lipase, for example, the microbial enzyme is a mycobacterial lipase. In certain embodiments, such compounds specifically inhibit enzyme activity with only moderate, or with minimal, or without any cytotoxicity effect to a cell or to an organism.

The present disclosure also provides for methods of detecting an enzyme, such as detecting a lipase including microbial lipases. Detection may be achieved with numerous protocols known to those of ordinary skill in the art such as including a tag that is or can be visualized. In certain embodiments, the method of detection is via fluorescence. In particular embodiments, a fluorescent tag can be introduced either at the phosphorus atom or at the C-5 carbon atom of certain structures provided herein. Such labeled compounds, when coupled with proteomic analysis, are contemplated to be powerful probes to identify-via for example 2D gel electrophoresis-mycobacterial proteins that react with the inhibitors. Thus, such compounds may be of value for understanding not only the molecular mechanisms involved in catalytic activities, such as lipase catalytic activity, but also for exploring associated physiological lipid pathways and sensing and detecting enzymes and/or organisms containing those enzymes.

Cyclophostin (FIG. 1: 1a) was previously isolated from *Streptomyces lavendulae* (strain NK 901093).[6] Cyclophostin showed extremely potent inhibitory activity against housefly acetylcholinesterase (AChE) with an $IC_{50}$ of 0.76 nM. It is characterized by a unique cyclic phosphate triester fused to a lactone ring. The bicyclic core also contains a unique vinylogous phosphate carbonic anhydride and chiral centers at both phosphorus and C-3a carbon atom. A series of structurally related natural products named the Cyclipostins (1c-l) were isolated from fermentation broths of *Streptomyces* sp. DSM 13381.7. The members of the Cyclipostins family vary in the structure of the lipophilic chain attached to the phosphate ester. Many members of this family possess strong inhibitory activity against hormone-sensitive lipase (HSL) with $IC_{50}$ values in the nanomolar range. The change from C16 alkyl to methyl phosphate switches selectivity from potent HSL inhibitor to potent AChE inhibitor, with little affinity for the other enzyme.

The lipophilic Cyclipostins have also been shown to block lipolysis in intact rat adipocytes by direct inhibition of hormone-sensitive lipase (HSL).[7b] A comparison of cell free and whole cell activity showed that the Cyclophostin are efficiently transported into the cell. Further studies also showed that Cyclipostins possess antimycobacterial activity.

Modifications can be introduced (FIG. 2: X, Y, Z, $R^1$, $R^2$, $R^3$ and $R^4$) to tailor specificity for a particular enzyme. This allows for the synthesis of a large variety of fully customizable monocyclic enolphosphonates substituted at the C-5 carbon position (R3 group). Furthermore, the methyl phosphonate and phosphates esters can be trans-esterified to give long chain ester compounds ($ZR^1$ chains, Z=O) analogous to Cyclipostins.

The total synthesis of the racemic Cyclophostin (1a,b),[9] Cyclipostins (1g, 1m),[9] and their phosphate (3c) and phosphonate (2a-l & 3a-b) analogs have been reported[10-13] (FIG. 3). Diastereomeric cis- and trans-monocyclic enolphosphonate analogs (2b-h) were previously screened against representative lipolytic enzymes belonging to distinct lipase families.[12] None of these enolphosphonates inhibited mammalian gastric and pancreatic lipases. However, *Fusarium solani* Cutinase and lipases from *M. tb* (Rv0183 and LipY) were all fully inactivated. The most potent inhibitors displayed a cis conformation (between H and OMe) and exhibited higher inhibitory activities than Orlistat, used as reference inhibitor,[5] towards the same enzymes (Table 1).

TABLE 1

Enzyme inhibition data[12,13] and antibacterial activities of the most active Cyclipostins & Cyclophostin analogs.

| Compounds | LipY $x_{150}{}^a$ | Rv0183 $x_{150}{}^a$ | Extracellular growth IC$_{50}$ (µM) | Intracellular macrophage growth IC$_{50}$ (µM) | CC$_{50}$ (µM) |
|---|---|---|---|---|---|
| Isoniazid$^d$ | N/A | N/A | 1.2 | 1.2 | >150 |
| Ethionamide$^d$ | N/A | N/A | 6.0 | 6.0 | 120 |
| Rifampin$^d$ | N/A | N/A | 0.01 | 2.9 | 24 |
| (±)2d(α) | >100 | 3.79 | No effect | 6.0 | >100 |
| (±)2e(α) | 22.7$^b$ (15.4$^c$) | 3.57$^b$ (1.24$^c$) | ≥100$^e$ | 4.0$^e$ | >100 |
| (±)2e(β) | 2.76$^b$ (1.64$^c$) | 1.13$^b$ (1.16$^c$) | 15-20$^e$ | 3.0$^e$ | >100 |
| (±)2f(α) | 6.14 | 2.44 | 30-50 | 4.0 | >100 |
| (±)2f(β) | 3.46 | 5.23 | >100 | 10.0 | >20 |
| (±)1g(α) | 0.50 | ND | 24.4 | No effect | >100 |
| (±)1m(β) | 0.51 | ND | 1.6 | No effect | >100 |
| (±)3c | 0.50 | ND | 0.5 | No effect | >100 |

Certain aspects of this disclosure provide for novel enolphosphonate and enolphosphate analogs of cyclophostin and cyclipostins and for methods of their production and use. In certain embodiments, these new compounds can be used as lipase inhibitors, for example, microbial lipase inhibitors such as mycobacterial lipase inhibitors. In certain embodiments, for example when attached to a tag moiety, these new compounds can be used in the detection of lipase inhibitors, for example, microbial lipase inhibitors such as mycobacterial lipase inhibitors. Certain compounds (monocyclic phosphonates and phosphates) are known inhibit Rv0183 and LipY from *M. tb*. Furthermore, these compounds were shown to exhibit significant anti-mycobacterial activity either in culture or in infected macrophages (Table 1). Certain monocyclic phosphonate analogs of 2 (with additional variations in R³) and monocyclic phosphate analogs of compound 3c (with variations in R¹) are disclosed herein for the exploration of the structure activity relationship (SAR) of these unique pharmacophores.

Figure 12:
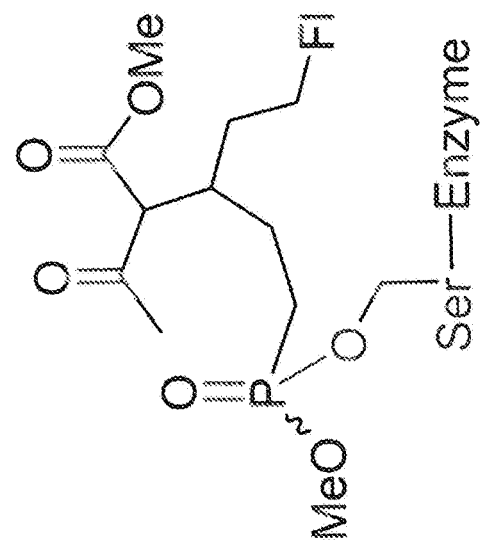
Figure 12:
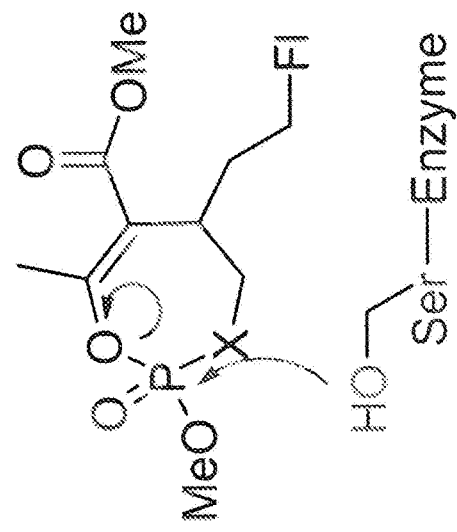

Certain aspects of this disclosure provide for compounds, and methods of making and using them, that react with an active site serine residue of an enzyme to form a covalent link, such as illustrated in FIG. 12. In certain embodiments, the enzyme is a hydrolase. In certain embodiments, the enzyme is a lipase such as a microbial lipase such as a mycobacterial lipase. In embodiments where a fluorescent label (also referred to interchangeably as a fluorescent tag or flurophore) is utilized, the adduct formed (e.g., fluorescently labeled compound plus the enzyme) can be visualized by fluorescence. Such compounds can be referred to as affinity probes.

Certain aspects of this disclosure provide for fluorescent labeled monocyclic enolphosphorus inhibitors and methods of making and using them. The synthetic pathways developed for obtaining the various phosphonate inhibitors allow for the introduction of a fluorescent tag suitable for the search for target enzymes. When fluorescently tagged inhibitors are used, the tagged enzyme becomes "visible" and can be detected and quantified on the basis of the fluorescent signal.[25] Fluorescently labeled phosphonates have proven useful as probes for sensitive and rapid detection of active proteins by one- or two-dimensional gel electrophoresis either in pure form or in complex proteome sample.[26] Numerous fluorophores useful as fluorescent tags are known by those of ordinary skill in the art that can be used to label compounds disclosed herein. Representative examples of fluorophores for fluorescently labeling compounds include the nitrobenzo-2-oxa-1,3-diazole (NBD) fluorophore (excitation/emission maxima at 470/530 nm) and the dansyl group. In certain embodiments, the inhibitors 1g(β), 2d(α), 2e(α,β), 2f(α,β) and 3c are fluorescently tagged.

Figure 9:
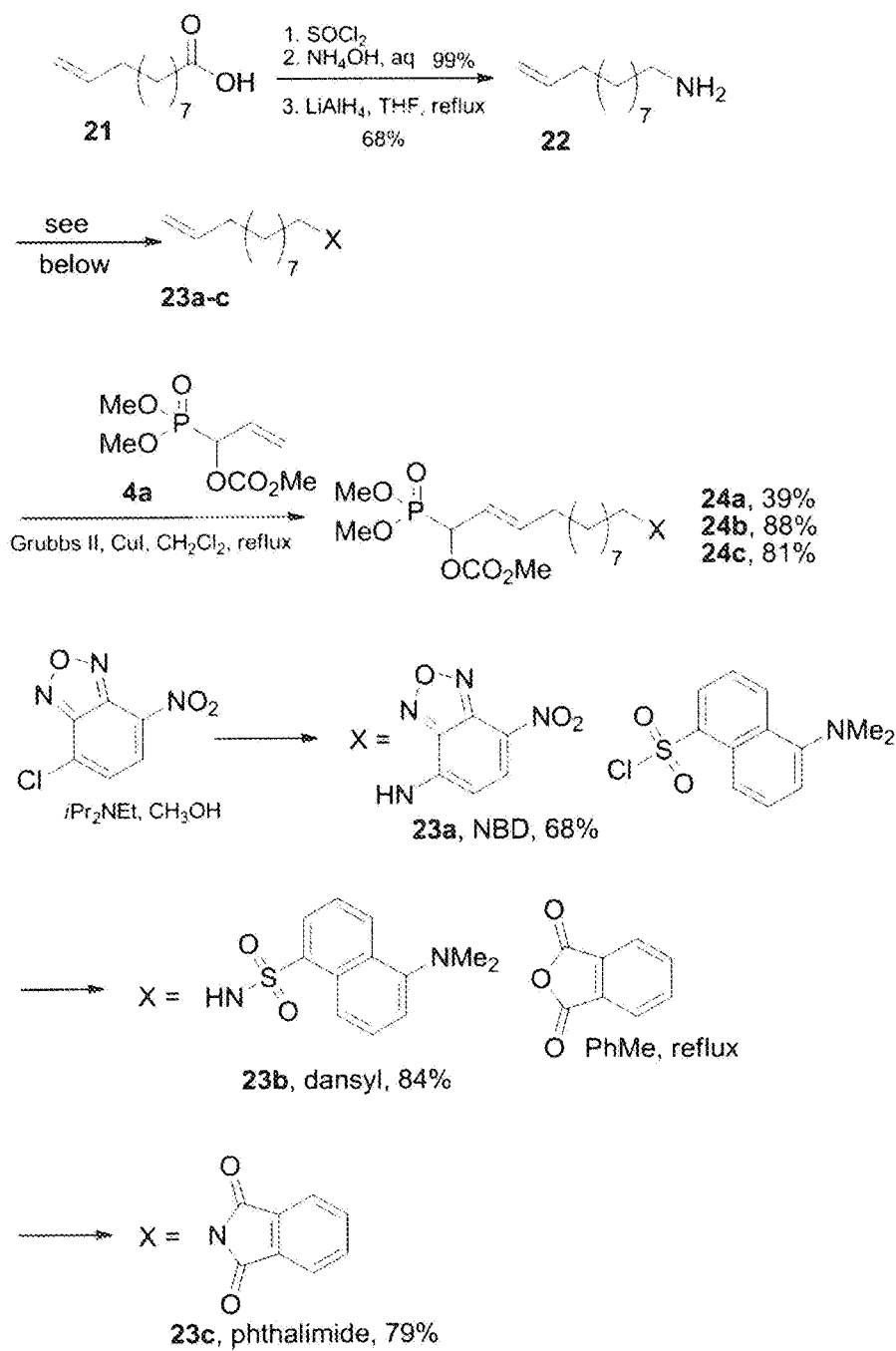

In certain aspects, cross-metathesis reaction between the fluorescently labeled olefins (23a)[28] and (23b) and 1-(dimethoxyphosphoryl)allyl methyl carbonate (4a) can produce precursor carbonates (24a and 24b) (FIG. 9: Scheme 6). In certain embodiments, a method of producing a compound comprises one or more of the steps shown in Scheme 6.

Figure 10:
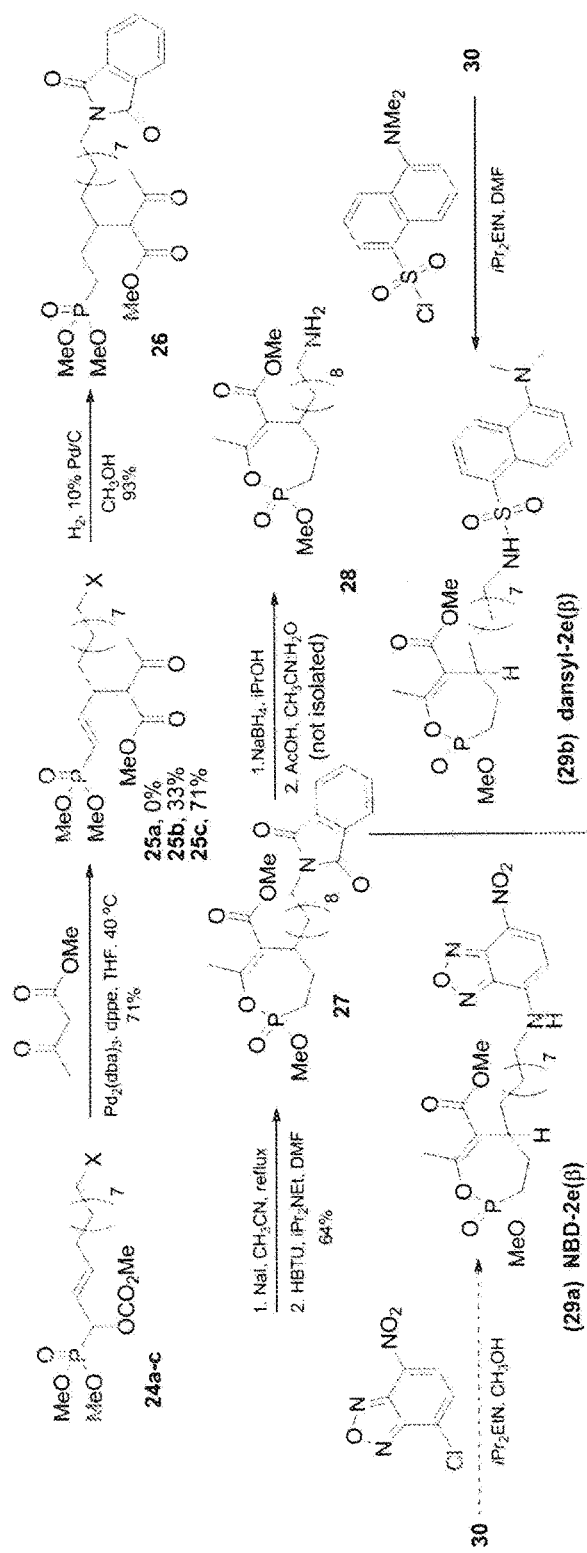
Figure 13:
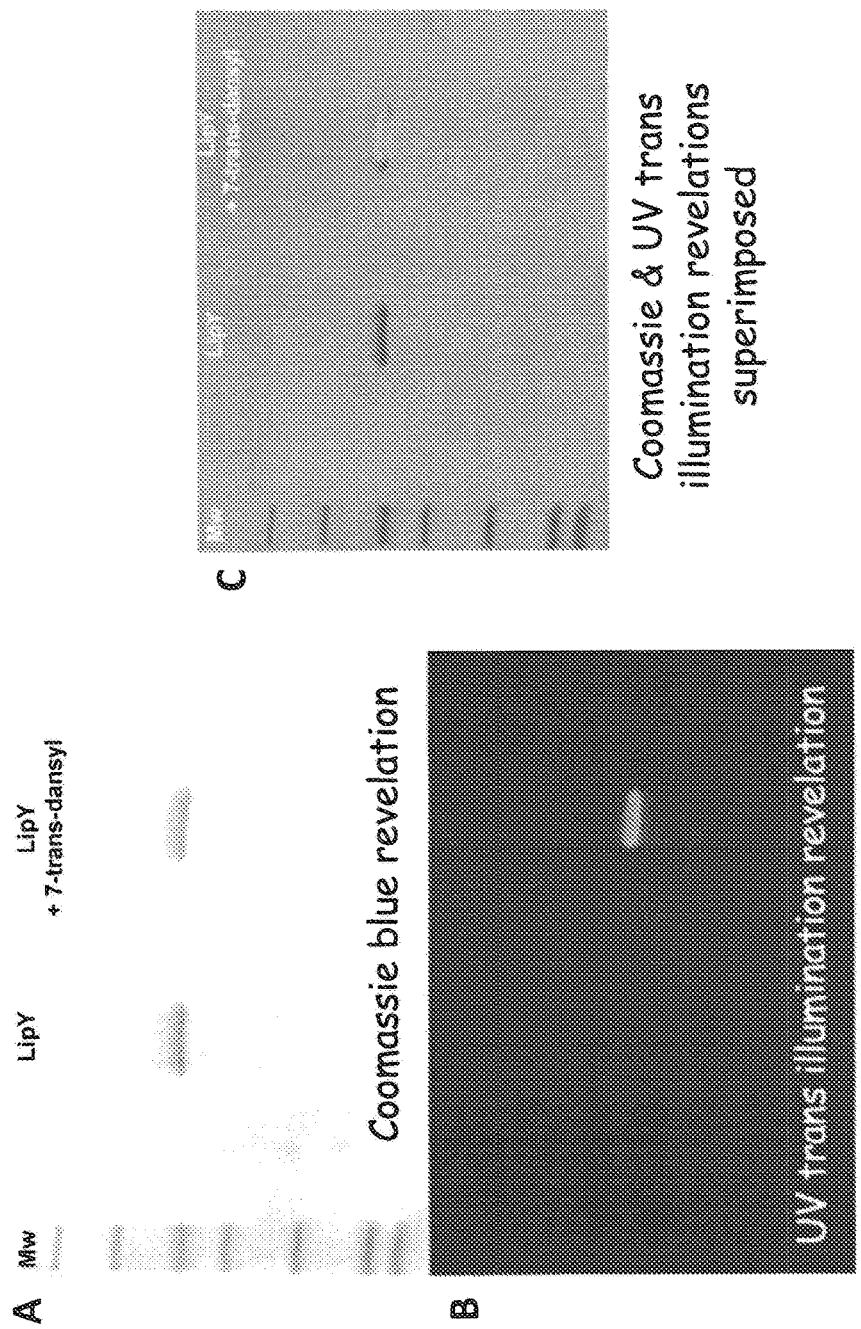

In certain aspects, phthalimide protected amino enolphosphonate (27) can be obtained in three additional steps from (25c) (FIG. 10: Scheme 7). Phthalimide can be removed using a two-step reaction sequence. Conversion of amine (28) to the dansyl amide (29b) was successful and this compound (29b) was shown to react with LipY giving an enzyme adduct that could observed by fluorescence on an electrophoresis gel (FIG. 13). Addition of the NBD group to amine (28) resulted in the formation of(29a), albeit at low yield. Although the NBD derivative (24a) did not participate in the palladium catalyzed substitution with methyl acetoacetate, both the dansyl and phthalimide protected compound (24b and 24c) (FIG. 10: Scheme 7) were reactive in the palladium catalyzed substitution. In certain embodiments, a method of producing a compound comprises one or more of the steps shown in Scheme 7. Certain embodiments provide for a compound comprising the structure:

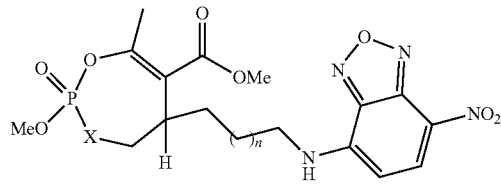

wherein n is any of 1 to 20 and wherein X is O or CH$_2$. In certain specific embodiments, X is CH$_2$. In certain specific embodiments, X is O. Certain embodiments provide for a compound comprising the structure:

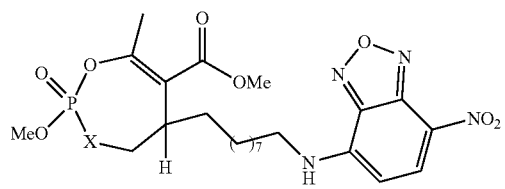

wherein X is O or CH$_2$. In certain specific embodiments, X is CH$_2$ (Scheme 7: (29a) NBD-2e(β)). In certain specific embodiments, X is O. Certain embodiments provide for a compound comprising the structure:

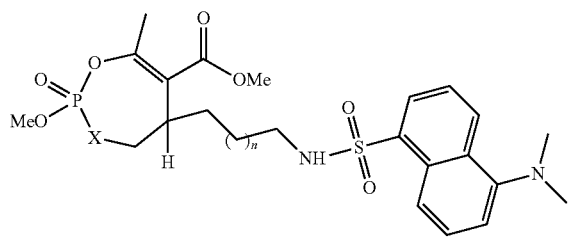

wherein n is any of 1 to 20 and wherein X is O or CH$_2$. In certain specific embodiments, X is CH$_2$. In certain specific embodiments, X is O. Certain embodiments provide for a compound comprising the structure:

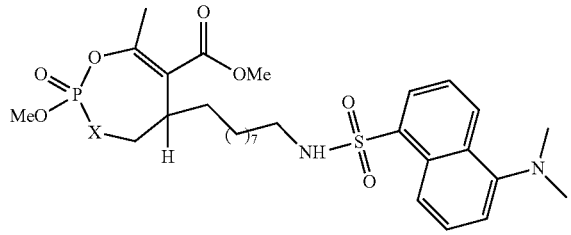

wherein X is O or CH$_2$. In certain specific embodiments, X is CH$_2$ (Scheme 7: (29b) dansyl-2e(β)). In certain specific embodiments, X is O.

Figure 11:
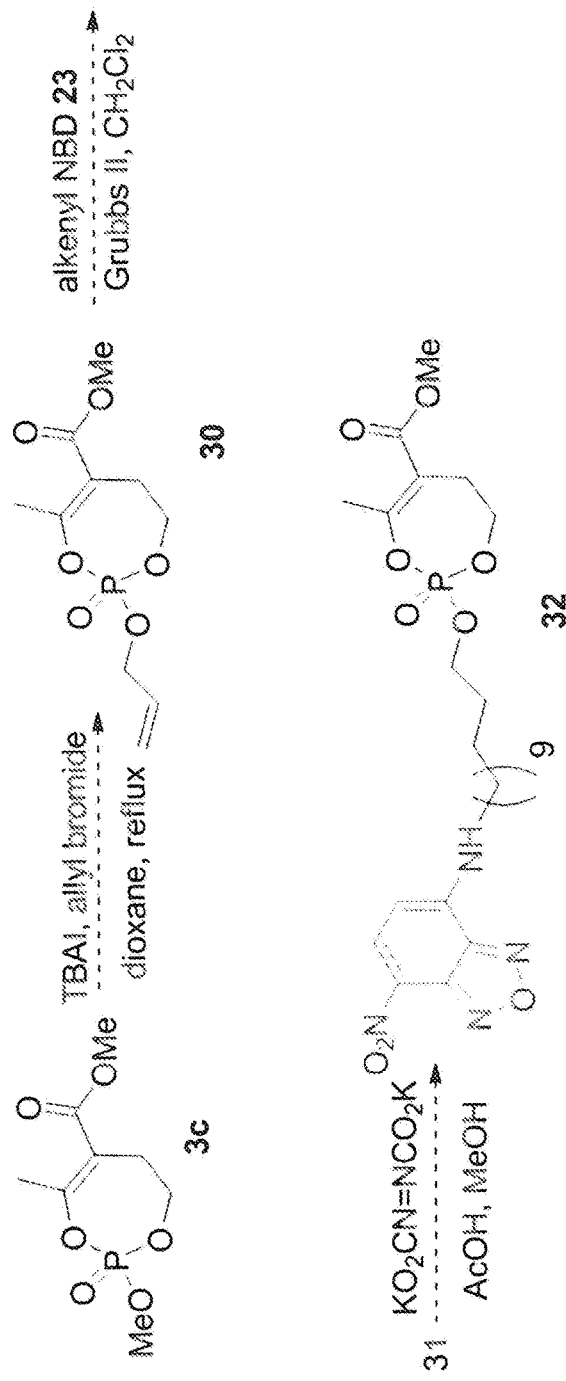

In certain aspects, a NBD or dansyl label can be placed on a phosphate or phosphonate ester moiety (FIG. 11: Scheme 8). In certain embodiments, a method of producing a compound comprises one or more of the steps shown in Scheme 8. In this pathway the methyl ester is first trans-esterified to the allyl ester (30), which is reacted with the NBD alkene (23) under standard cross metathesis conditions (FIG. 9: Scheme 6).[28] It is contemplated that the alkene (31) will be reduced to give (32) with diimide to avoid unwanted reduction of the NBD with heterogeneous transition metal catalysts and hydrogen.[29] It is contemplated that similar procedures will be used for compounds with different chain lengths. Certain embodiments provide for a compound comprising the structure:

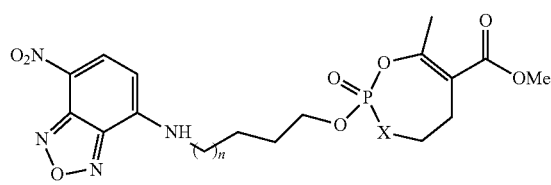

wherein n is any of 1 to 20 and X is O or CH$_2$. In certain specific embodiments, X is O. In certain specific embodiments, X is CH$_2$. Certain embodiments provide for a compound comprising the structure:

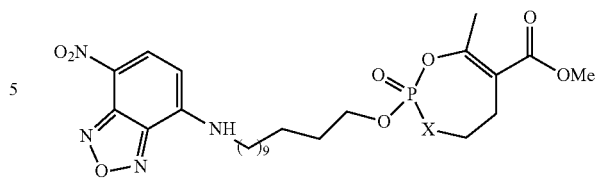

wherein X is O or CH$_2$. In certain specific embodiments, X is O (Scheme 8: (32)). In certain specific embodiments, X is CH$_2$. Certain embodiments provide for a compound comprising the structure:

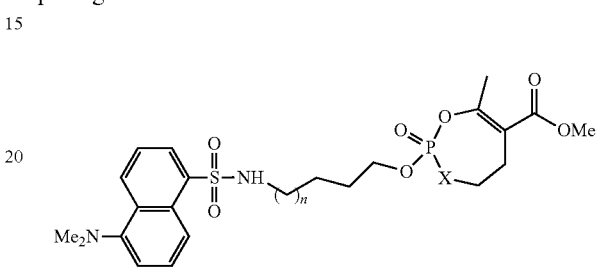

wherein n is any of 1 to 20 and X is O or CH$_2$. In certain specific embodiments, X is O. In certain specific embodiments, X is CH$_2$. Certain embodiments provide for a compound comprising the structure:

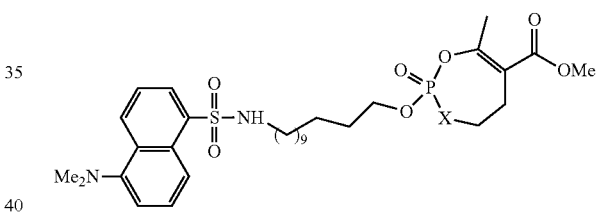

wherein X is O or CH$_2$. In certain specific embodiments, X is O. In certain specific embodiments, X is CH$_2$.

Certain aspects provide for a series of fluorescently labeled phosphonate or phosphate compounds including those disclosed above and below. Such probes can be used, for example, for the search of target enzymes. Such probes can be used, for example, for the ex vivo search of target enzymes. In certain embodiments, the fluorescently labeled compound comprises a cyclic enolphosphonate or cyclic enolphosphate and a fluorescent label or tag (fluorophore). In certain embodiments, the compound has one of the following structures:

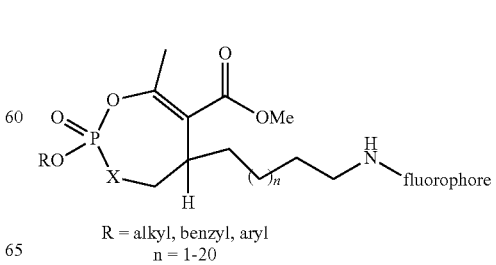

R = alkyl, benzyl, aryl
n = 1-20

-continued

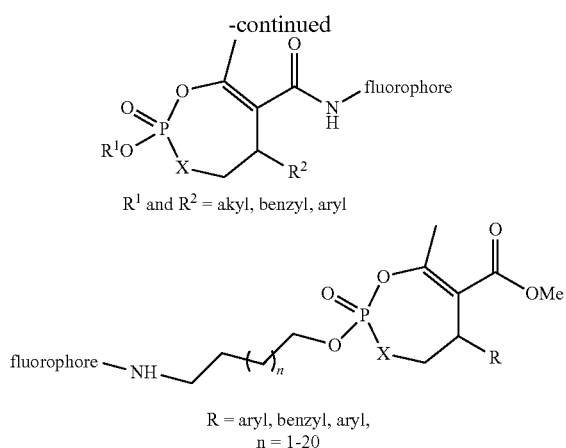

R¹ and R² = akyl, benzyl, aryl

R = aryl, benzyl, aryl,
n = 1-20 wherein X is O or CH$_2$. In certain specific embodiments, the fluorophore or fluorescent label is a nitrobenzo-2oxa-1,3-diazole (NBD) fluorophore such as a compound having one of the following structures:

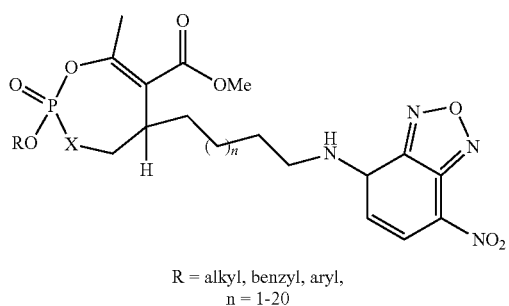

R = alkyl, benzyl, aryl,
n = 1-20

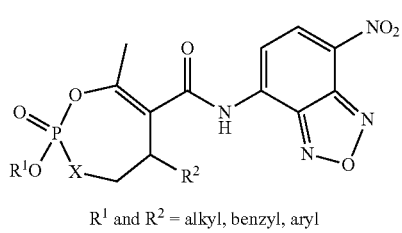

R¹ and R² = alkyl, benzyl, aryl

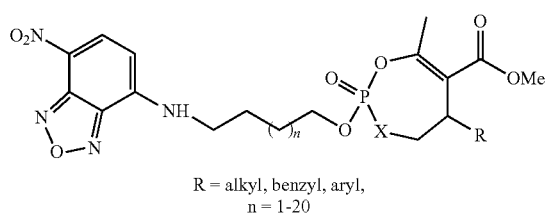

R = alkyl, benzyl, aryl,
n = 1-20 wherein X is O or CH$_2$. In certain specific embodiments, X is O. In certain specific embodiments X is CH$_2$.

In certain aspects, in any of the above structures, the attached fluorophore or fluorescent label is a dansyl fluorophore instead of NBD.

In certain embodiments, the compound has the structure:

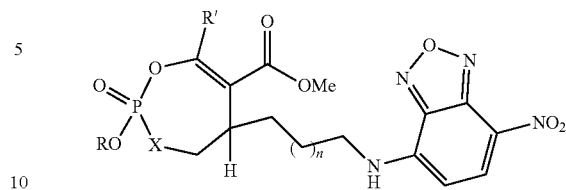

wherein n is any of 1 to 20; wherein R is alkyl, benzyl, or aryl; and wherein X is O or CH$_2$. R' can be any of from one carbon to twenty carbon atoms, thus, R' is any one of C1 to C20. In certain specific embodiments, X is O. In certain specific embodiments, X is CH$_2$. In certain specific embodiments, R' is a methyl group. In certain specific embodiments, n is 7.

In certain embodiments, the compound has the structure:

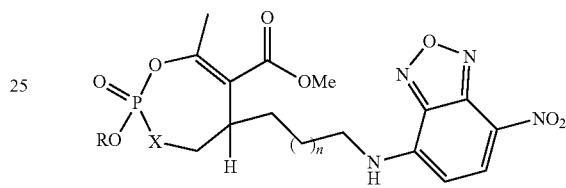

wherein n is any of 1 to 20; wherein R is alkyl, benzyl, or aryl; and wherein X is O or CH$_2$. In certain specific embodiments, X is O. In certain specific embodiments, X is CH$_2$. In certain specific embodiments, n is 7.

In certain embodiments, the compound has the structure:

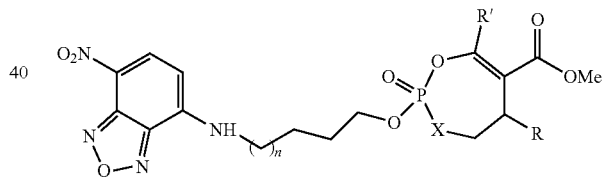

wherein n is any of 1 to 20; wherein R is alkyl, benzyl, or aryl; and wherein X is O or CH$_2$. R' can be any of from one carbon to twenty carbon atoms, thus, R' is any one of C1 to C20. In certain specific embodiments, X is O. In certain specific embodiments, X is CH$_2$. In certain specific embodiments, R' is a methyl group. In certain specific embodiments, n is 9.

In certain embodiments, the compound has the structure:

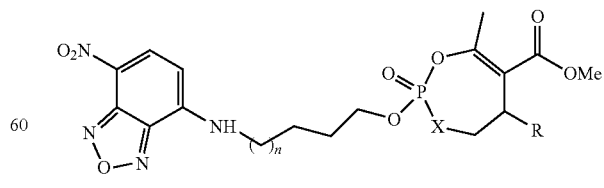

wherein n is any of 1 to 20; wherein R is alkyl, benzyl, or aryl; and wherein X is O or CH$_2$. In certain specific embodiments, X is O. In certain specific embodiments, X is CH$_2$. In certain specific embodiments, n is 9.

In certain embodiments, the compound has the structure:

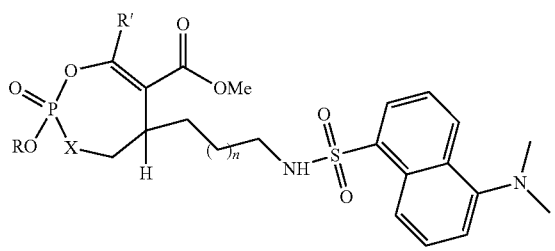

wherein n is any of 1 to 20; wherein R is alkyl, benzyl, or aryl; and wherein X is O or $CH_2$. R' can be any of from one carbon to twenty carbon atoms, thus, R' is any one of C1 to C20. In certain specific embodiments, X is O. In certain specific embodiments, X is $CH_2$. In certain specific embodiments, R' is a methyl group. In certain specific embodiments, n is 7.

In certain embodiments, the compound has the structure:

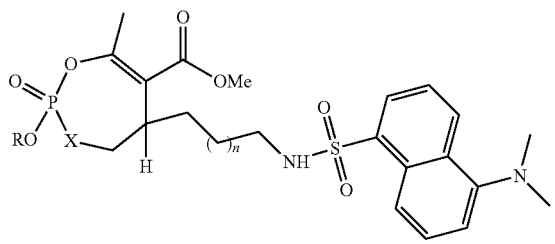

wherein n is any of 1 to 20; wherein R is alkyl, benzyl, or aryl; and wherein X is O or $CH_2$. In certain specific embodiments, X is O. In certain specific embodiments, X is $CH_2$. In certain specific embodiments, n is 7.

In certain embodiments, the compound has the structure:

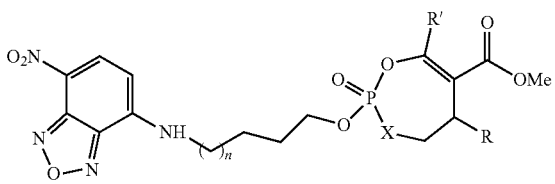

wherein n is any of 1 to 20; wherein R is alkyl, benzyl, or aryl; and wherein X is O or $CH_2$. R' can be any of from one carbon to twenty carbon atoms, thus, R' is any one of C1 to C20. In certain specific embodiments, X is O. In certain specific embodiments, X is $CH_2$. In certain specific embodiments, R' is a methyl group. In certain specific embodiments, n is 9.

In certain embodiments, the compound has the structure:

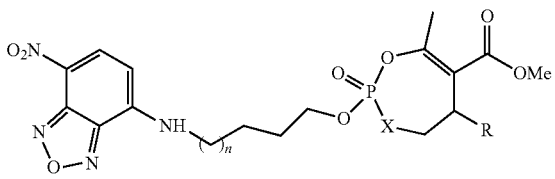

wherein n is any of 1 to 20; wherein R is alkyl, benzyl, or aryl; and wherein X is O or $CH_2$. In certain specific embodiments, X is O. In certain specific embodiments, X is $CH_2$. In certain specific embodiments, n is 9.

In certain aspects, a fluorescent label can be placed at various positions on a monocyclic phosphonate or phosphate core using minor modifications of synthetic methods described herein.

Certain aspects provide for labeled inhibitor compounds in enantiopure form. Such compounds in enantiorpure form can be obtained by adapting racemic pathways to asymmetric synthesis such as described herein for compound 2e.[13]

The following disclosed embodiments are merely representative. Thus, specific structural, functional, and procedural details disclosed in the following examples are not to be interpreted as limiting.

EXAMPLES

Example 1. Anti-Mycobacterial Activity

The anti-mycobacterial activity of enolphosphonates 2a-h and enolphosphates 3a-c on the extracellular or intracellular growth of *M. tb* was determined. The compounds were evaluated with the *M. tb*. H37Rv-GFP strain using a high-content screening assay based on the fluorescence measurement of eGFP-expressing bacteria.[14-17] In vitro growth of *M. tb* H37Rv-GFP was monitored by directly measuring GFP fluorescence after 5 days at 37° C. in presence of increasing concentrations of compounds. Intracellular growth of *M. tb* H37Rv-GFP was also assessed following a 5-day exposure of Raw 264.7 infected murine macrophage cell lines to the different compounds. Confocal images were then recorded on an automated fluorescent ultrahigh-throughput microscope.[15,16] The percent of infected cells and the number of cells which are the two parameters extracted from image analysis,[16,17] allowed to estimate the values of both $IC_{50}$ (compound concentration leading to 50% growth inhibition) and $CC_{50}$ (compound concentration leading to 50% cell toxicity). As shown in Table 1, two types of inhibitory effects have been obtained. Analogs 2e(α), 2f(β) are able to act both on extracellular growth as well as in infected macrophages with moderate (15-50 μM) to good (3-4 μM) $IC_{50}$ values, respectively. In contrast, compounds 2d(α), 2e(α) and 2f(β) have a clear effect only on infected macrophages; whereas 1g, 1m and 3a displayed antibacterial activity with $IC_{50}$ up to the nanomolar range ($IC_{50}$≅500 nM for 3a). These eight inhibitors did not exhibit toxicity towards the macrophages themselves. More particularly, both isomers of 2e were found to exhibit similar or even higher activities ($IC_{50}$) towards intramacrophagic bacilli than first line antibiotics used as references.

Without being bound by theory, it is thought that such findings suggest several modes of action of these related compounds (extracellular vs. intracellular) and probably several target enzymes, including, but not exclusively, lipolytic enzymes. Although classical phosphonate (P-F and P-OAr) compounds are well known and extensively studied lipase inhibitors, they tend to lack specificity and are structurally simple which limits SAR studies. Preliminary results obtained with this new class of cyclic enolphosphonate and enolphosphate compounds, suggest that such specific inhibitors represent useful probes to decipher the mode of action of serine hydrolases from *M. tb* in normal and foamy infected macrophages.

Example 2. Synthesis of Phosphonate Analogs of Cyclophostin.[10-13]

Figure 1:
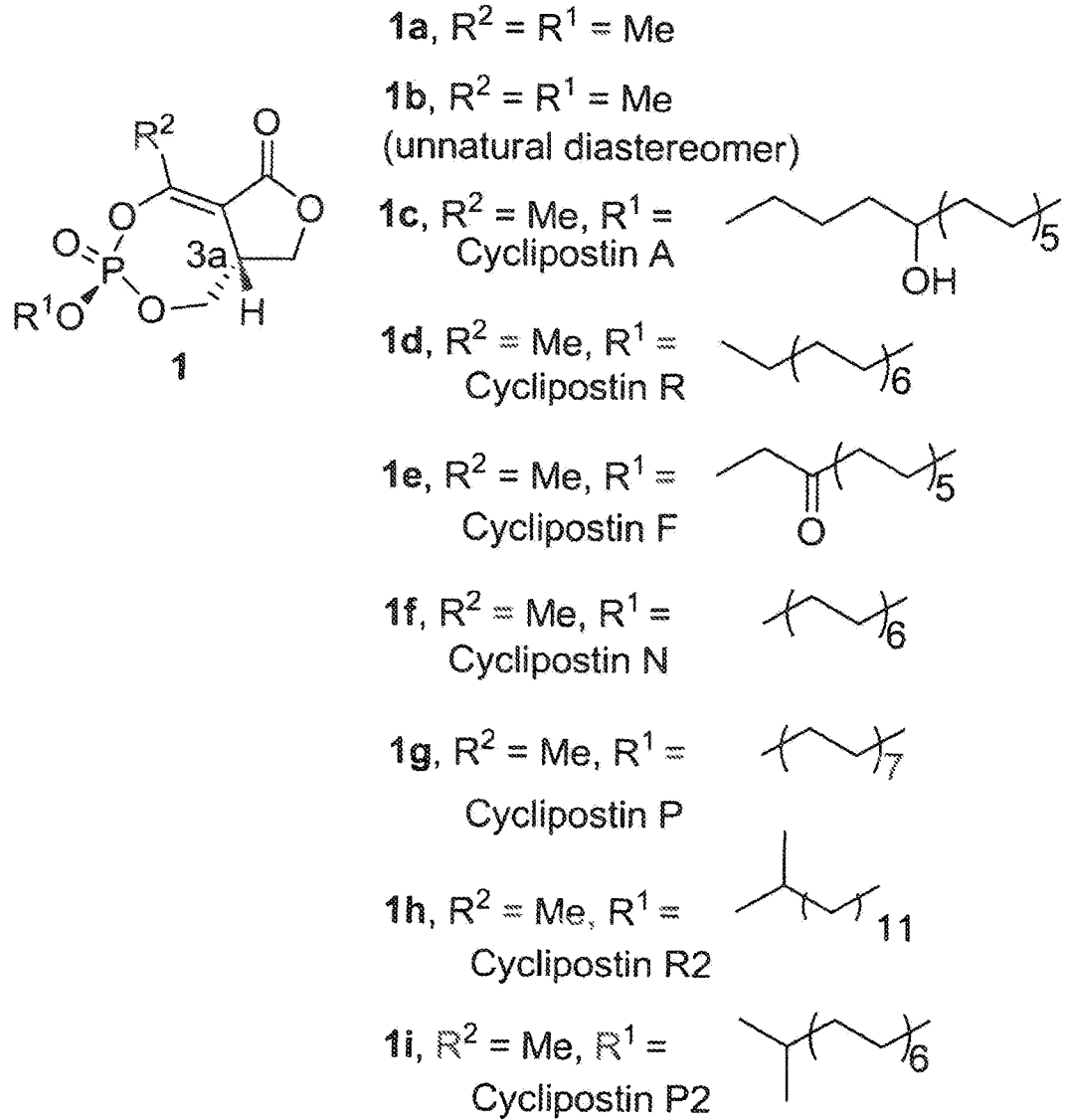
FIG. 1 shows Cyclophostin and the structurally related Cyclipostins.
Figure 1:
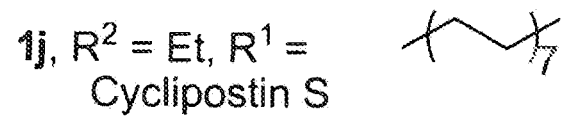
Figure 1:
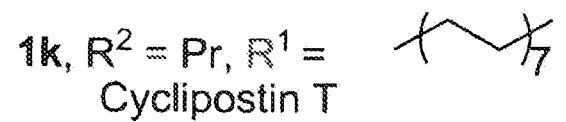
Figure 1:
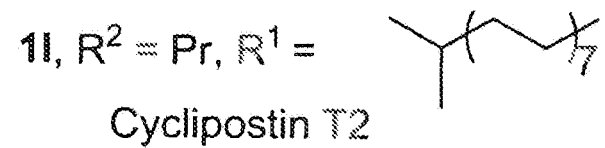
Figure 2:
FIG. 2 shows potential modifications to Cyclophostin.
Figure 3:
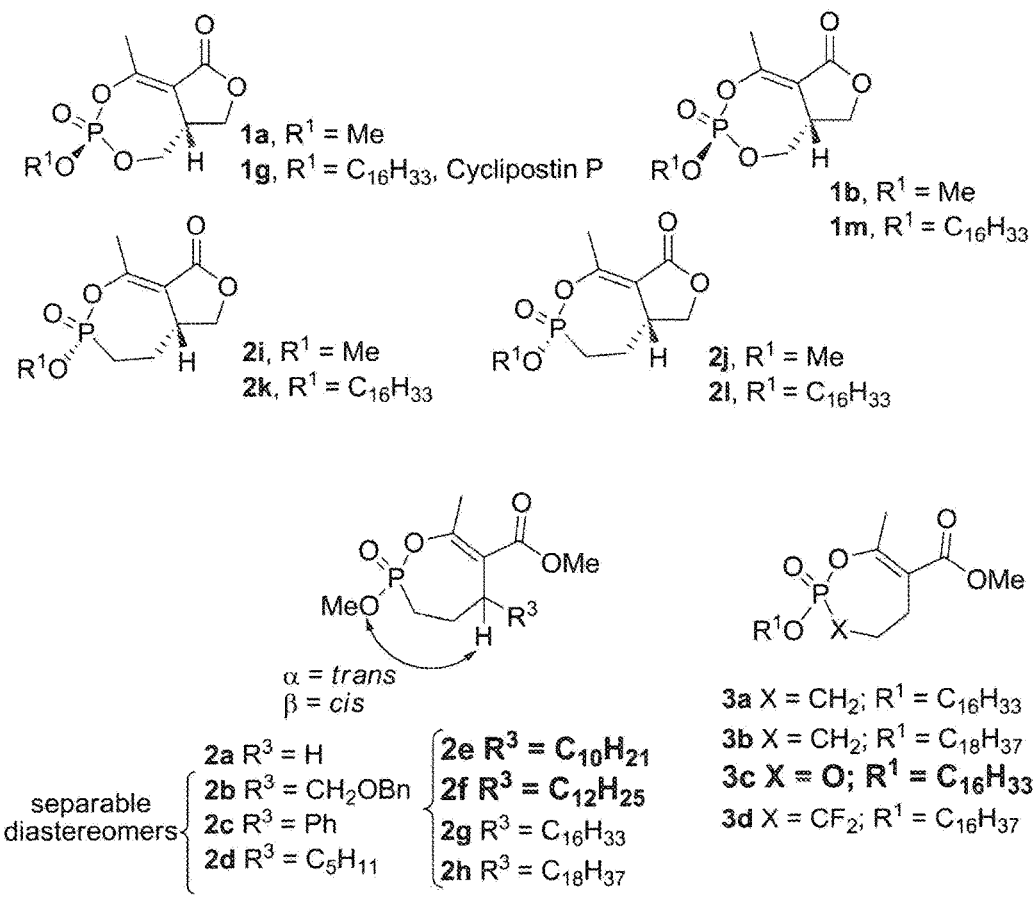
FIG. 3 shows Cyclophostin, Cyclipostins, and their phosphate and phosphonate analogs.
Figure 4:
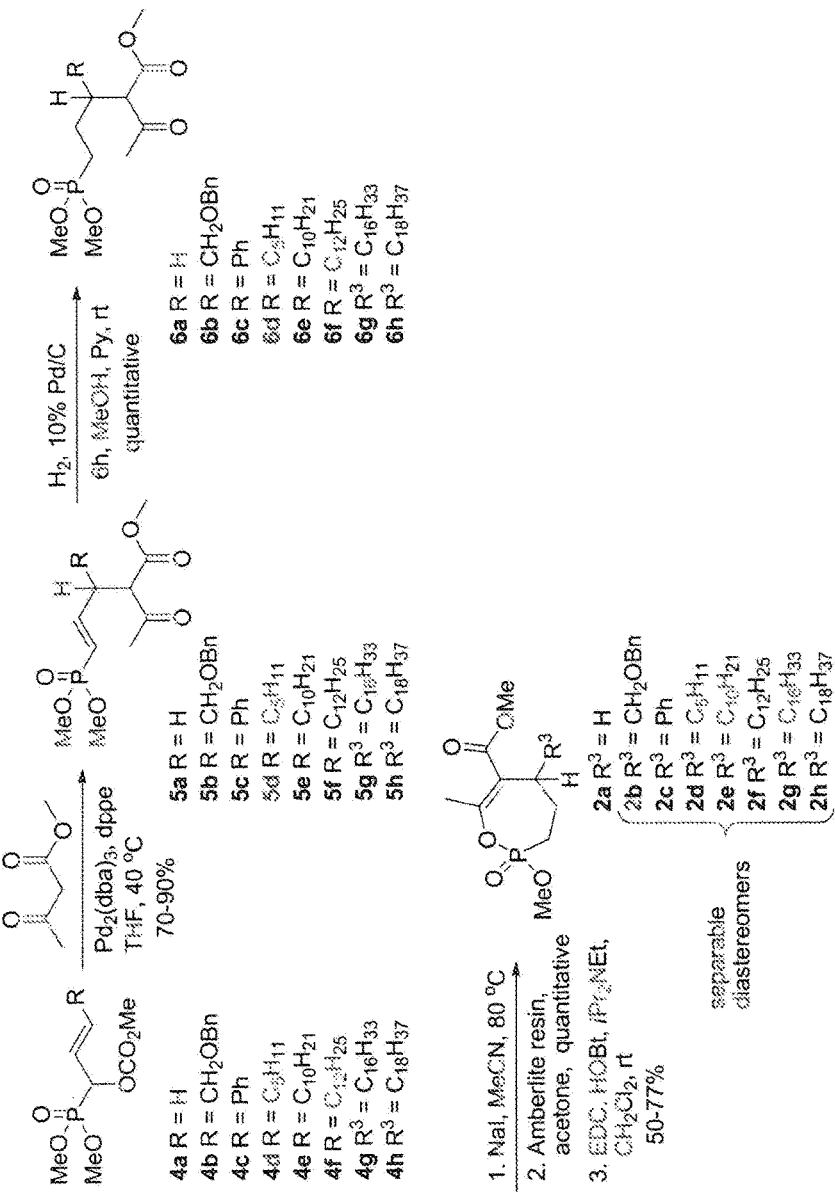
Figure 5:
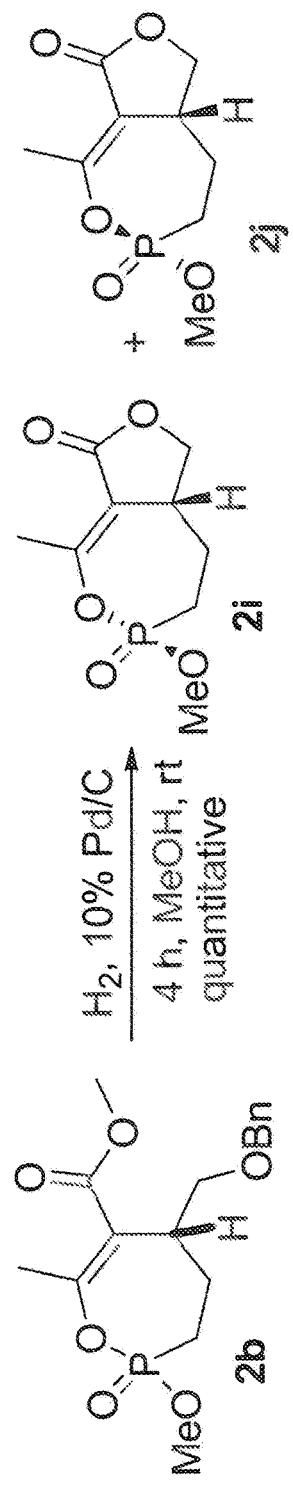

A general (enantioselective)[13] approach to a family of phosphonate analogs (2) of Cyclophostin was developed utilizing the palladium catalyzed substitution reaction of phosphono allylic carbonates (FIG. 4: Scheme 1). The palladium catalyzed reaction of methyl acetoacetate with the allylic carbonates (4) gave the vinyl phosphonates (5) in good yield. Hydrogenation of the vinyl phosphonate (5) gave the saturated phosphonate (6), which after selective demethylation, protonation of the resulting salt, and cyclization gave the monocyclic enolphosphonates (2). Selective debenzylation of phosphonate (2b) with hydrogen over palladium on carbon (FIG. 5: Scheme 2) resulted in rapid lactonization to give the diastereomeric phosphonate isosteres of Cyclophostin (2i, j).[10]

Example 3. Synthesis of the Cyclipostins and Phosphonate Analogs.[9,12]

Figure 6:
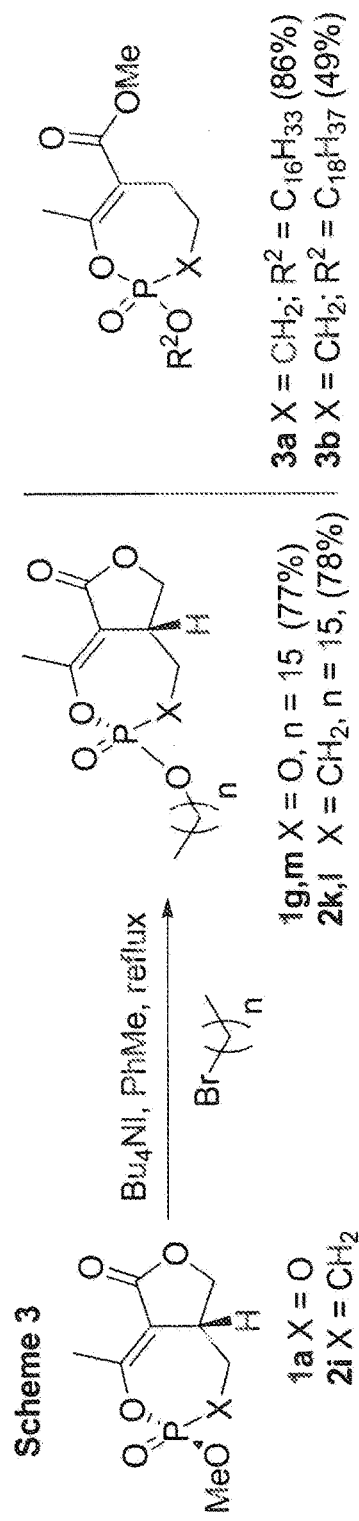

Conversion of Cyclophostin (1a) and phosphonate analog (2i) to the diastereomeric Cyclipostins (1g,m) and analogs (2k,l) was achieved via in situ selective cleavage of the methyl phosphonate ester with tetrabutylammonium iodide (TBAI) and re-alkylation with a long chain alkyl bromide (FIG. 6: Scheme 3). This reactions sequence was also successful with the monocyclic phosphonate analog (2a) giving long chain esters (3a,b).

Example 4. Monocyclic Phosphate Analogs

Figure 7:
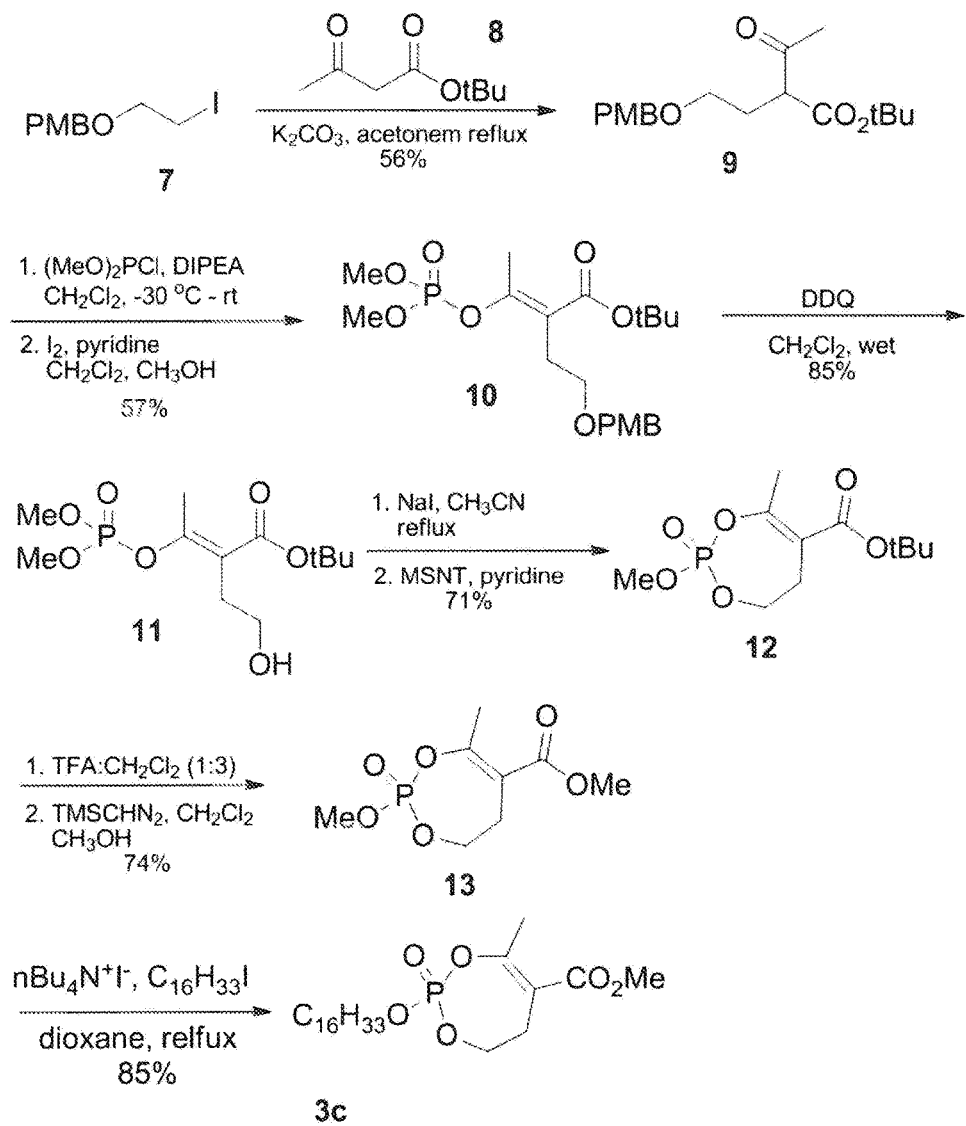

In order to optimize the observed antibacterial activity towards M. tb (Table 1), the synthesis of the monocyclic phosphate derivative (3c) was completed. β-Ketoester (9) was prepared by alkylation[20] of t-butyl acetoacetate (8) with iodide (7)[21] (FIG. 7: Scheme 4). The tert-butyl ester was chosen to minimize the risk of lactonization upon deprotection to the alcohol. Reaction of the β-ketoester (9) with dimethyl chlorophosphite, followed by oxidation of crude material with $I_2$ and methanol gave enolphosphate (10). The PMB ether protecting group was removed with DDQ to give alcohol (11). Demethylation and cyclization using 1-mesitylene-sulfonyl-3-nitrotriazole (MSNT) gave monocyclic tert-butyl ester (12). Cleavage of the tert-butyl moiety with TFA in anhydrous conditions was surprisingly effective and is a testament to the surprising stability of the enolphosphate bond. The resulting carboxylic acid was treated with $TMSCHN_2$ to give cyclic phosphate methyl ester (13) (FIG. 7: Scheme 4). Trans-esterification gave the hexadecyl ester (3c).

Example 5. Monocyclic Difluorophosphonate Analogs

Figure 8:
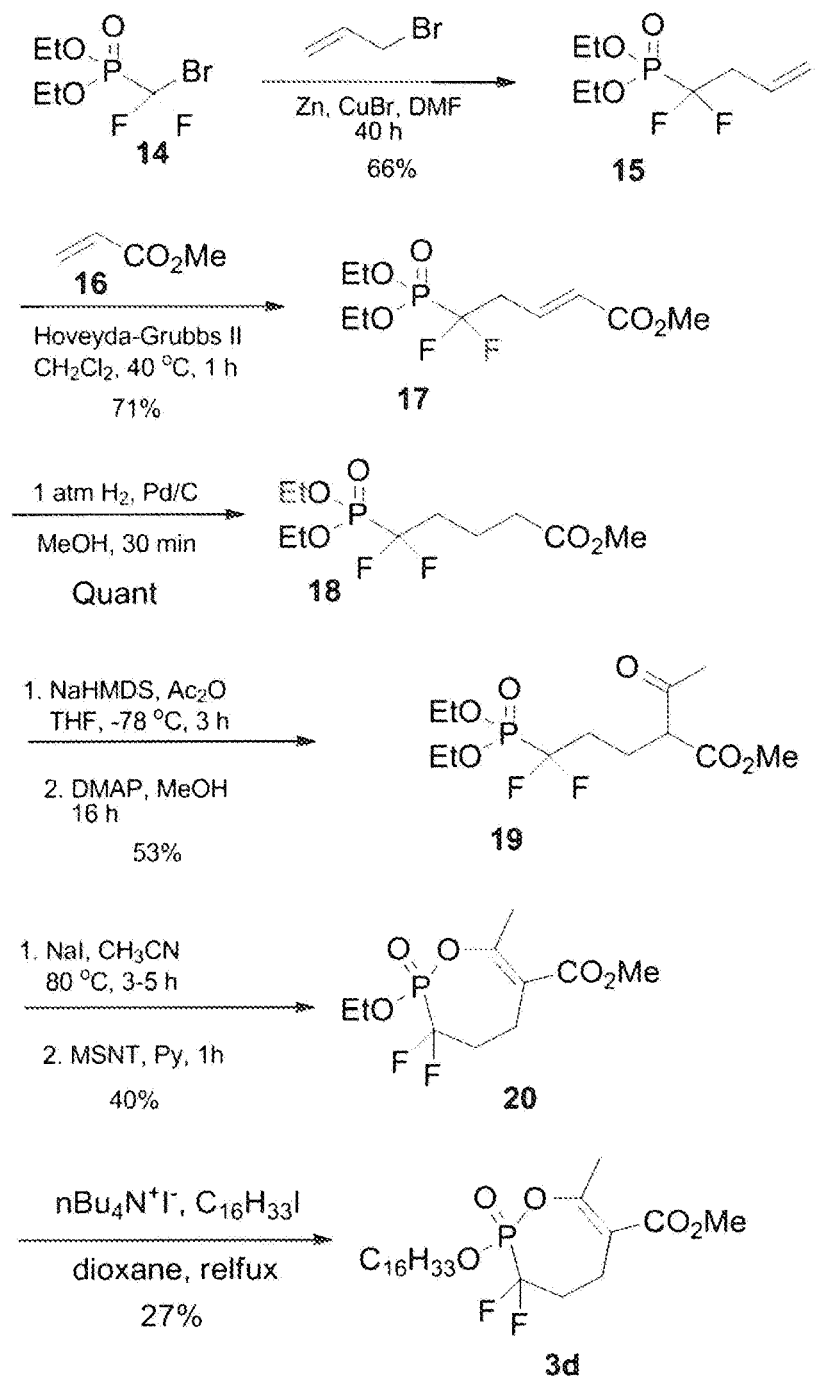

Monocyclic difluoro analogs (3d) were prepared. The (allyl-difluoro)phosphonate (15) was prepared by reaction of the cuprate of diethyl (bromodifluoromethyl)phosphonate (14) with allyl bromide (FIG. 8: Scheme 5).[24] Cross methathesis with methyl acrylate (16) using Hoveyda-Grubbs II catalyst gave unsaturated ester (17) which was hydrogenated to the saturated ester (18).

Using conditions previously employed for the synthesis of Cyclophostin analogs, formation of an enolate, trapping with acetic anhydride and hydrolysis of the crude product (containing some enolacetate) gave the β-ketoester (19). Selective de-ethylation was accomplished by treatment with NaI in refluxing acetonitrile. Cyclization with 1-(Mesitylene-2-sulfonyl)-3-nitro-1,2,4-triazole (MSNT), produced cyclic α,α-difluorophosphonate (20) in usable quantities. Trans-esterification gave the hexadecyl ester (3d). The difluoro enolphosphonates (20 and 3d) were considerably less stable than the corresponding phosphonates (2a and 3a) resulting in lower yields after isolation by chromatography. The $xi_{50}$ values reached towards LipY inhibition were >40 and 3.42 for 20 and 3d, respectively.

Example 6. Specificity and Selectivity of Pure Mycobacterial Lipolytic Enzymes Chemical compounds disclosed herein will be tested for their inhibitory properties towards lipolytic enzymes belonging to the HSL,[5d,32] Cutinase[33], and MGL[34] families by using several specific and robust routine enzyme inhibition assays[35,36] developed at the EIPL lab. Around 20 lipolytic enzymes are already available in pure recombinant forms and have already been biochemically characterized. Orlistat, the best characterized and non-selective inhibitor of serine hydrolases, can be used as a reference inhibitor. To exclude any non-competitive covalent inhibition, tryptic digestion of the lipase-inhibitor adduct will be performed, and the peptide mass fingerprint (PMF) thus obtained by ESI-Q TOF mass spectrometry will allow to confirm the specific covalent binding of the inhibitor to the catalytic serine residue.[12]

Example 7. Mycobacterial Viability

The minimal inhibitory concentration (MIC) of newly designed lipase inhibitors disclosed herein will be determined by agar or broth dilution methods.[5d] The mycobacterial growth will be monitored by scoring colony forming units (CFU) during treatment. These experiments will be performed with BCG and M. tb MC27000 strains.[37] The most efficient inhibitors can be used for further cytotoxicity assays on host macrophages (Example 8).

Example 8. Cytotoxicity Assays on Non-Infected Macrophages and Anti-Mycobacterial Activity on Infected Macrophages Macrophages (bone marrow-derived mouse macrophages, BMDM and human macrophages) will be exposed to increasing concentrations of selected lipolytic enzyme inhibitors of interest (from 0 to 100 μM). The viability and morphological integrity of macrophages will be monitored at selected time points during the treatment by light microscopy and cell lysis will be evaluated by measurement of the released lactate dehydrogenase (CytoTox 96® Non-Radioactive Cytotoxicity Assay, Promega). The cytotoxic concentration ($CC_{50}$) leading to 50% cell death of all chemical compounds will then be determined.

Candidate inhibitors, such as those that appear non-cytotoxic, can be selected for anti-mycobacterial experiments. BMDM will be infected, such as with the M. bovis BCG (BCG) fluorescent strain. Once the bacteria are actively replicating (e.g., six days later), cells will be exposed to various concentrations of the inhibitors. At selected time points thereafter, cells will be fixed and processed for electron microscopy and the effect on cells viability and bacterial clearance will be examined.

While the invention has been described in connection with example embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

REFERENCES

1. WHO. (2013) http://www.who.int/tb/publications/global_report/en/index.html
2. a) "Safety and efficacy of MVA85A, a new tuberculosis vaccine, in infants previously vaccinated with BCG: a randomised, placebo-controlled Phase 2b trial" Tameris, M. D.; Hatherill, M.; Landry, B. S.; Scriba, T. J.; Snowden, M. A.; Lockhart, S.; Shea, J. E.; McClain, J. B.; Hussey, G. D.; Hanekom, W. A.; Mahomed, H.; McShane, H. *Lancet* 2013, 381(9871), 1021; b) "Antituberculosis Drug Research: A Critical Overview" Beena and Rawat, D. S. *Med. Res. Rev.* 2013, 33: 693; c) "Advances in the development of new tuberculosis drugs and treatment regimens" Zumla, A.; Nahid, P.; Cole, S. T. *Nat Rev Drug Discov* 2013, 12, 388-404; d) "Towards a new combination therapy for tuberculosis with next generation benzothiazinones" Makarov, V.; Lechartier, B.; Zhang, M.; Neres, J.; van der Sar, A. M.; Raadsen, S. A.; Hartkoorn, R. C.; Ryabova, O. B.; Vocat, A.; Decosterd, L. A.; Widmer, N.; Buclin, T.; Bitter, W.; Andries, K.; Pojer, F.; Dyson, P. J.; Cole, S. T. *EMBO Mol Med* 2014, 6, 372-383. e) www.newtbdrugs.org/downloads/pipeline-slide/WGND_Global_TB_Drug_and Discovery_Pipelines-AUG2014.ppt.
3. a) "Foamy macrophages from tuberculous patients' granulomas constitute a nutrient-rich reservoir for *M. tuberculosis* persistence" Peyron, P.; Vaubourgeix, J.; Poquet, Y.; Levillain, F.; Botanch, C.; Bardou, F.; Daffe, M.; Emile, J. F.; Marchou, B.; Cardona, P. J.; de Chastellier, C.; Altare, F., *PLoS Pathog* 2008, 4, e1000204. b) "Foamy macrophages and the progression of the human tuberculosis granuloma" Russell, D. G.; Cardona, P. J.; Kim, M. J.; Allain, S.; Altare, F. *Nature immunology* 2009, 10, 943-948. c) "*Mycobacterium tuberculosis*-driven targeted recalibration of macrophage lipid homeostasis promotes the foamy phenotype" Singh, V.; Jamwal, S.; Jain, R.; Verma, P.; Gokhale, R.; Rao, K. V., *Cell host & microbe* 2012, 12, 669-681. d) "*Mycobacterium tuberculosis* keto-mycolic acid and macrophage nuclear receptor TR4 modulate foamy biogenesis in granulomas: a case of a heterologous and noncanonical ligand-receptor pair" Dkhar, H. K.; Nanduri, R.; Mahajan, S.; Dave, S.; Saini, A.; Somavarapu, A. K.; Arora, A.; Parkesh, R.; Thakur, K. G.; Mayilraj, S.; Gupta, P. *J. Immunol.* 2014, 193, 295-305. e) "Reversible lipid accumulation and associated division arrest of *Mycobacterium avium* in lipoprotein-induced foamy macrophages may resemble key events during latency and reactivation of tuberculosis" Caire-Brändli, I.; Papadopoulos, A.; Malaga, W.; Marais, D.; Canaan, S.; Thilo, L.; de Chastellier, C. *Infect. Immun.* 2014, 82, 476-490.
4. a) "Restraining mycobacteria: role of granulomas in mycobacterial infections" Saunders, B. M.; Cooper, A. M. *Immunol Cell Biol* 2000, 78, 334; b) "Evolution of granulomas in lungs of mice infected aerogenically with *Mycobacterium tuberculosis*" Cardona, P. J.; Llatjos, R.; Gordillo, S.; Diaz, J.; Ojanguren, I.; Ariza, A.; Ausina, V. *Scand J Immunol* 2000, 52, 156.
5. a) "Mycobacterial lipolytic enzymes: A gold mine for tuberculosis research" Dedieu, L.; Serveau-Avesque, C.; Kremer, L.; Canaan, S. *Biochimie* 2013, 95, 66. b) "Identification and structural characterization of an unusual mycobacterial monomeromycolyl-diacylglycerol" Kremer, L.; de Chastellier, C.; Dobson, G.; Gibson, K. J. C.; Bifani, P.; Balor, S.; Gorvel, J. P.; Locht, C.; Minnikin, D. E.; Besra, G. S. *Mol. Microbiol.* 2005, 57, 1113; c) "Inhibitors of an essential mycobacterial cell wall lipase (Rv3802c) as tuberculosis drug leads" West, N. P.; Cergol, K. M.; Xue, M.; Randall, E. J.; Britton, W. J.; Payne, R. J. *Chem Commun (Camb)* 2011, 47, 5166; d) "MmPPOX Inhibits *Mycobacterium tuberculosis* Lipolytic Enzymes Belonging to the Hormone-Sensitive Lipase Family and Alters Mycobacterial Growth" Delorme, V.; Diomandé, S. V.; Dedieu, L.; Cavalier, J.-F.; Carrière, F.; Kremer, L.; Leclaire, J.; Fotiadu, F.; Canaan, S. *PLoS ONE* 2012, 7, e46493.
6. a) "Insecticidal Organophosphates: Nature Made Them First" Neumann, R.; Peter, H. H. *Experimentia* 1987, 43, 1235; b) "Cyclophostin, Acetylcholinesterase Inhibitor from *Streptomyces lavendulae*" Kurokawa, T.; Suzuki, K.; Hayoka, T.; Nakagawa, T.; Izawa, T.; Kobayhsi, M.; Harada, N. J. *J. Antibiot.* 1993, 46, 1318.
7. a) "Cyclipostins: Novel Hormone-Sensitive Lipase Inhibitors from *Streptomyces* sp. DSM 13381. I. Taxonomic Studies of the Producer Microorganism and Fermentation Results" Wink, J.; Schmidt, F.-R.; Seibert, G.; Aretz, W. *J. Antibiot.* 2002, 55, 472; b) "Cyclipostins: Novel Hormone-Sensitive Lipase Inhibitors from *Streptomyces* sp. DSM 13381. II. Isolation, Structure Elucidation and Biological Properties" Vertesy, L.; Beck, B.; Bronstrup, M.; Ehrlich, K.; Kurz, M.; Muller, G.; Schummer, D.; Seibert, G. *J. Antibiot.* 2002, 55, 480.
8. "Treating mycobacterial infections with cyclipostins" Seibert, G.; Toti, L.; Wink, J. WO/2008/025449.
9. a) "The First Total Synthesis of (±) Cyclophostin and (±) Cyclipostin P: Inhibitors of the Serine Hydrolases Acetyl Cholinesterase and Hormone Sensitive Lipase" Malla, R. K.; Bandyopadhyay, S.; Spilling, C. D.; Dutta S.; Dupureur, C. M. *Organic Letters* 2011, 13, 3094-3097. b) "Rat Hormone Sensitive Lipase Inhibition by Cyclipostins and their Analogs" Vasilieva, E.; Dutta S.; Malla, R. K.; Martin, B. P.; Spilling, C. D.; Dupureur, C. M. *Biorg. Med Chem.* 2015, in press http://dx.doi.org/10.1016/j.bmc.2015.01.028.
10. "Synthesis and Biological Evaluation of a Phosphonate Analog of the Natural Acetyl Cholinesterase Inhibitor Cyclophostin" Bandyopadhyay, S.; Dutta, S.; Spilling, C. D.; Dupureur, C. M.; Rath, N. P. *J. Org. Chem.* 2008, 73, 8386-8391.
11. "Synthesis and Kinetic Analysis of Some Phosphonate Analogs of Cyclophostin as Inhibitors of Human Acetylcholinesterase" Dutta, S.; Malla, R. K.; Bandyopadhyay, S.; Spilling, C. D.; Dupureur, C. M. *Bioorg. Med. Chem.* 2010, 18, 2265-2274.
12. "Synthesis and Kinetic Evaluation of Cyclophostin and Cyclipostins Phosphonate Analogs as Selective and Potent Inhibitors of Microbial Lipases" Point, V.; Malla, R. K.; Diomande, S.; Martin, B. P.; Delorme, V.; Carriere, F.; Canaan, S.; Rath, N. P.; Spilling, C. D.; Cavalier, J.-F. *J. Med Chem.* 2012, 55, 10204-10219.
13. "Enantioselective Inhibition of Microbial Lipolytic Enzymes by Nonracemic Monocyclic Enolphosphonate Analogs of Cyclophostin" Point, V.; Malla, R. K.; Carri- ère, F.; Canaan, S.; Spilling, C. D.; Cavalier, J. F. *J. Med Chem.* 2013, 56, 4393-4401.
14. "High-content screening in infectious diseases" Brodin, P., and Christophe, T. *Curr Opin Chem Biol* 2011, 15, 534;
15. "High-content imaging of *Mycobacterium tuberculosis*-infected macrophages: an in vitro model for tuberculosis drug discovery" Christophe, T.; Ewann, F.; Jeon, H. K.; Cechetto, J.; Brodin, P. *Future Med Chem* 2010, 2, 1283.
16. "High content screening identifies decaprenyl-phosphoribose 2' epimerase as a target for intracellular antimycobacterial inhibitors" Christophe, T., Jackson, M., Jeon, H. K., Fenistein, D., Contreras-Dominguez, M., Kim, J., Genovesio, A., Carralot, J. P., Ewann, F., Kim, E. H., Lee, S. Y., Kang, S., Seo, M. J., Park, E. J., Skovierova, H., Pham, H., Riccardi, G., Nam, J. Y., Marsollier, L., Kempf, M., Joly-Guillou, M. L., Oh, T., Shin, W. K., No, Z., Nehrbass, U., Brosch, R., Cole, S. T., and Brodin, P. *PLoS Pathog* 2009, 5, e1000645.
17. "Ethionamide boosters: synthesis, biological activity, and structure-activity relationships of a series of 1,2,4-oxadiazole EthR inhibitors" Flipo, M., Desroses, M., Lecat-Guillet, N., Dirie, B., Carette, X., Leroux, F., Piveteau, C., Demirkaya, F., Lens, Z., Rucktooa, P., Villeret, V., Christophe, T., Jeon, H. K., Locht, C., Brodin, P., Deprez, B., Baulard, A. R., and Willand, N. *J Med Chem* 2011, 54, 2994.
18. a) "Chemical Probes for Profiling Fatty Acid Associated Proteins in Living Cells" Raghavan, A.; Charron, G.; Flexner, J.; Hang, H. C.; *Bioorg. Med. Chem. Lett.* 2008, 18, 5982; b) "Activity Based Protein Profiling: The Serine Hydrolases" Liu, Y.; Patricelli, M. P.; Cravatt, B. F. *PNAS* 1999, 96, 14694; c) "Cannabinoid CB1 Receptor Chemical Affinity Probes: Methods Suitable for Preparation of Isopropyl [11,12-$^3$H] Dodecyl fluorophosphonate [11,12-$^3$H] Dodecanesulfonyl Fluoride" Segall, Y.; Quistad, G. B.; Casida, J. E. *Synth. Commun.* 2003, 33, 2151. d) "Supported inhibitor for fishing lipases in complex biological media and mass spectrometry identification" Delorme, V.; Raux, B.; Puppo, R.; Leclaire, J.; Cavalier, J.-F.; Marc, S.; Kamarajugadda, P.-K.; Buono, G.; Fotiadu, F.; Canaan, S.; Carrière, F. *Biochimie* 2014, 107, 124-134.
19. a) "Irreversible Inhibition of Serine Proteases by Peptide Derivatives of (α-Aminoalkyl)phosphonate Diphenyl Esters" Oleksyszyn, J.; Powers, J. C. *Biochemistry* 1991, 30, 485; b) "Synthesis of Phophonopeptides as Thrombin Inhibitors" Wang, C.-L. J.; Taylor, T. L.; Mical, A. J.; Spitz, S.; Reilly, T. M.; *Tetrahedron Lett.* 1992, 33, 7667; c) "Development of Irreversible Diphenyl Phosphonate Inhibitors for Urokinase Plasminogen Activator" Joossen, J.; Van der Veken, P.; Lambeir, A.-M.; Augustyns, K.; Haemers, A. *J. Med. Chem.* 2004, 47, 2411; d) "γ-(Monophenyl)phosphono glutamate Analogues as Mechanism-based Inhibitors of γ-Glutamyl Transpeptidase" Han, L.; Hiratake, J.; Tachi, N.; Suzuki, H.; Kumagai, H.; Sakata, K. *Bioorg. Med. Chem.* 2006, 14, 6043; e) "New Potent Cathepsin G Phosphonate Inhibitors" Sienczyk, M.; Lesner, A.; Wysocka, M.; Legowska, A.; Pietrusewicz, E.; Rolka, K.; Oleksyszyn, J. *Bioorg. Med. Chem.* 2008, 16, 8863.
20. a) Chehade, K. A. H.; Kiegiel, K.; Isaacs, R. J.; Pickett, J. S.; Bowers, K. E.; Fierke, C. A.; Andres, D. A.; Spielman, H. P. *J. Am. Chem. Soc.* 2002, 28, 8206-8219. b) Mulholland, N. P.; Pattenden, G.; Walters, I. A. S. *Org. Biomol. Chem.* 2008, 6, 2782-2789.
21. "Total Synthesis of Salicylihalamides A and B" Herb, C.; Bayer, A.; Maier, Martin E. *Chem. Eur. J.* 2004, 10, 5649.
22. a) Blackburn, G. M.; Taylor, G. E.; Tattershall, R. H.; Thatcher, G. R. J.; McLennan, A. "Phosphonate Analogues of Biological Phosphates" in Biophosphates and their Analogues—Synthesis, Structure, Metabolism and Activity, Bruzik, K. S.; Stec, W. J., Eds., Elsevier Science Publishers B. V., Amsterdam, Netherlands, 1987, 451; b) "Phosphonates as Analogues of Natural Phosphates" Engel, R. *Chem. Rev.* 1977, 77, 349; c) "Phosphonates as Analogues of Biological Phosphates" Blackburn, G. M.; *Chem. Ind* (London) 1981, 134.
23. a) "Monofluoro- and Difluoro-methylenebisphosphonic Acids: Isopolar Analogues of Pyrophosphoric Acid" Blackburn, G. M.; England, D. A.; Kolkmann, F. *Chem. Commun.* 1981, 930; b) "Fluorination of Methanediphosphonate Esters by Perchloryl Fluoride Synthesis of Fluoromethanediphosphonic acid and Difluoromethanediphosphonic Acid" McKenna, C. E.; Shen, P. *J. Org. Chem.* 1981, 46, 4573; c) "Fluorinated Phosphonates: Synthesis and Biomedical Application" Romanenko, V. D.; Kukhar, V. P. *Chem. Rev.* 2006, 106, 3868; d) "(α-Monofluoroalkyl)phosphonates: a Class of Isoacidic and "Tunable" Mimics of Biological Phosphates" Berkowitz, D. B.; Bose, M. *J. Fluorine Chem.* 2001, 112, 13.
24. "Allylations of [(diethoxyphosphinyl)difluoromethyl] zinc bromide as a convenient route to 1,1-difluoro-3-alkenephosphonates" Burton, D. J.; Sprague, L. G.; *J. Org. Chem.* 1989, 54, 613. (b) "Structural-based design and synthesis of novel 9-deazaguanine derivatives having a phosphate mimic as multi-substrate analogue inhibitors for mammalian PNPs" Hikishima, S.; Hashimoto, M.; Magnowska, L.; Bzowska, A.; Yokomatsu, T. *Bioorg. Med. Chem.* 2010, 18, 2275.
25. "Novel Fluorescent Phosphonic Acid Esters for Discrimination of Lipases and Esterases" Schmidinger, H.; Birner-Gruenberger, R.; Riesenhuber, G.; Saf, R.; Susani-Etzerodt, H.; Hermetter, A. *ChemBioChem,* 2005, 6, 1776.
26. "The lipolytic proteome of mouse adipose tissue" Birner-Gruenberger, R.; Susani-Etzerodt, H.; Waldhuber, M.; Riesenhuber, G.; Schmidinger, H.; Rechberger, G.; Kollroser, M.; Strauss, J. G.; Lass, A.; Zimmermann, R.; Haemmerle, G.; Zechner, R.; Hermetter, A. Mol Cell Proteomics 2005, 4, 1710.
27. a) "A versatile library of activity-based probes for fluorescence detection and/or affinity isolation of lipolytic enzymes" Susani-Etzerodt, H.; Schmidinger, H.; Riesenhuber, G.; Birner-Gruenberger, R.; Hermetter, A. *Chem Phys Lipids* 2006, 144, 60. b) Walker, J. "The Dansyl Method for Identifying N-Terminal Amino Acids". In *Basic Protein and Peptide Protocols*, Walker, J., Ed. Humana Press: 1994; Vol. 32, pp 321-328. c) Walker, J. "The Dansyl-Edman Method for Peptide Sequencing". In *Basic Protein and Peptide Protocols*, Walker, J., Ed. Humana Press: 1994; Vol. 32, pp 329-334.
28. "Versatile synthetic method for sphingolipids and functionalized sphingosine derivatives via olefin cross metathesis" Yamamoto T, Hasegawa H, Hakogi T, Katsumura S. *Org. Lett.* 2006, 8, 5569.
29. "Allylic Hydroxy Phosphonates: Versatile Chiral Building Blocks" De la Cruz, A.; He, A.; Thanavaro, A.; Yan, B.; Spilling, C. D.; Rath, N. P. *J. Organometal. Chem.* 2005, 690, 2577-2592.
30. a) "Conjugate Addition of Grignard Reagents to Ethyl Acrylate" Liu, S.-H. *J. Org. Chem.* 1977, 42, 3209; b) "Cu(I) Tol-BINAP-Catalyzed Enantioselective Michael Reactions of Grignard Reagents and Unsaturated Esters" Wang, S.-Y.; Ji, S.-J.; Loh, T.-P. *J. Am. Chem. Soc.* 2007, 129, 276.

31. "Salinipostins A-K, Long-Chain Bicyclic Phosphotriesters as a Potent and Selective Antimalarial Chemotype" Schulze, C. J.; Navarro, G.; Ebert, D.; DeRisi, J.; Linington, R. G. *J. Org. Chem.* 2015, asap DOI: 10.1021/jo5024409.

32. a) "Expression and characterization of the protein Rv1399c from *Mycobacterium tuberculosis*" Canaan, S.; Maurin, D.; Chahinian, H.; Pouilly, B.; Durousseau, C.; Frassinetti, F.; Scappuccini-Calvo, L.; Cambillau, C.; Bourne, Y. *Eur. J. Biochem.* 2004, 271, 3953. b) "*Mycobacterium tuberculosis* Lipolytic Enzymes as Potential Biomarkers for the Diagnosis of Active Tuberculosis" Brust, B.; Lecoufle, M.; Tuaillon, E.; Dedieu, L.; Canaan, S.; Valverde, V.; Kremer.; L. *PLoS ONE* 2011, 6, e25078.

33. "Two cutinase-like proteins secreted by *Mycobacterium tuberculosis* show very different lipolytic activities reflecting their physiological function" Schue, M.; Maurin, D.; Dhouib, R.; Bakala N'Goma, J. C.; Delorme, V.; Lambeau, G.; Carriere, F.; Canaan, S. *FASEB J* 2010, 24, 1893.

34. a) "Characterization of an exported monoglyceride lipase from *Mycobacterium tuberculosis* possibly involved in the metabolism of host cell membrane lipids" Côtes, K.; Dhouib, R.; Douchet, I.; Chahinian, H.; De Caro, A.; Carriere, F.; Canaan, S. *Biochem J.* 2007, 408, 417; b) "A monoacylglycerol lipase from *Mycobacterium smegmatis* Involved in bacterial cell interaction" Dhouib, R.; Laval, F.; Carriere, F.; Daffe, M.; Canaan, S. J Bacteriol 2010, 192, 4776.

35. "Covalent inactivation of lipases" Ransac, S.; Gargouri, Y.; Marguet, F.; Buono, G.; Beglinger, C.; Hildebrand, P.; Lengsfeld, H.; Hadváry, P.; Verger, R. *Methods in Enzymology* 1997, 286, 190.

36. "Method for the High-Speed Screening of Lipase Activity and/or Lipase Inhibitors in Biological Samples and in Culture Media" Cavalier, J.-F.; Carrière, F. WO/2013/007570.

37. "*Mycobacterium tuberculosis* ΔRD1 ΔpanCD: A safe and limited replicating mutant strain that protects immunocompetent and immunocompromised mice against experimental tuberculosis" Sambandamurthy, V. K.; Derrick, S. C.; Hsu, T.; Chen, B.; Larsen, M. H.; Jalapathy, K. V.; Chen, M.; Kim, J.; Porcelli, S. A.; Chan, J.; Morris, S. L.; Jacobs Jr., W. R. *Vaccine* 2006, 24(37-39), 6309.

38. a) "Inhibition of mycolic acid transport across the *Mycobacterium tuberculosis* plasma membrane" Grzegorzewicz, A. E.; Pham, H.; Gundi, V. A. K. B.; Scherman, M. S.; North, E. J.; Hess, T.; Jones, V.; Gruppo, V.; Born, S. E. M.; Aacute, J. K. A. K.; Chavadi, S. S.; Morisseau, C.; Lenaerts, A. J.; Lee, R. E.; McNeil, M. R.; Jackson, M. *Nat. Chem. Biol.* 2012, 8, 334-341. b) "Identification of novel inhibitors of *M. tuberculosis* growth using whole cell based high-throughput screening" Stanley, S. A.; Kazyanskaya, E.; Aquadro, J. A.; Silvis, M.; Gomez, J.; Hung, D. T. *ACS Chemical Biology* 2012, 7, 1377-1384.

"Synthesis and Biological Evaluation of a Phosphonate Analog of the Natural Acetyl Cholinesterase Inhibitor Cyclophostin" Bandyopadhyay, S.; Dutta, S.; Spilling, C. D.; Dupureur, C. M.; Rath, N. P. *J. Org. Chem.* 2008, 73, 8386-8391.

"Synthesis and Kinetic Analysis of Some Phosphonate Analogs of Cyclophostin as Inhibitors of Human Acetylcholinesterase" Dutta, S.; Malla, R. K.; Bandyopadhyay, S.; Spilling, C. D.; Dupureur, C. M. *Bioorg. Med. Chem.* 2010, 18, 2265-2274.

"Synthesis and Kinetic Evaluation of Cyclophostin and Cyclipostins Phosphonate Analogs as Selective and Potent Inhibitors of Microbial Lipases" Point, V.; Malla, R. K.; Diomande, S.; Martin, B. P.; Delorme, V.; Carriere, F.; Canaan, S.; Rath, N. P.; Spilling, C. D.; Cavalier, J.-F. *J. Med Chem.* 2012, 55, 10204-10219.

"Enantioselective Inhibition of Microbial Lipolytic Enzymes by Nonracemic Monocyclic Enolphosphonate Analogs of Cyclophostin" Point, V.; Malla, R. K.; Carrière, F.; Canaan, S.; Spilling, C. D.; Cavalier, J. F. *J. Med Chem.* 2013, 56, 4393-4401.

Synthesis and Biological Evaluation of a Phosphonate Analog of the Natural Acetyl Cholinesterase Inhibitor Cyclophostin" Bandyopadhyay, S.; Dutta, S.; Spilling, C. D.; Dupureur, C. M.; Rath, N. P. *J. Org. Chem.* 2008, 73, 8386-8391.

Synthesis and Biological Evaluation of a Phosphonate Analog of the Natural Acetyl Cholinesterase Inhibitor Cyclophostin" Bandyopadhyay, S.; Dutta, S.; Spilling, C. D.; Dupureur, C. M.; Rath, N. P. *J. Org. Chem.* 2008, 73, 8386-8391.

"The First Total Synthesis of (±) Cyclophostin and (±) Cyclipostin P: Inhibitors of the Serine Hydrolases Acetyl Cholinesterase and Hormone Senstive Lipase" Malla, R. K.; Bandyopadhyay, S.; Spilling, C. D.; Dutta S.; Dupureur, C. M. *Organic Letters* 2011, 13, 3094-3097.

"Rat Hormone Senstive Lipase Inhibition by Cyclipostins and their Analogs" Vasilieva, E.; Dutta S.; Malla, R. K.; Martin, B. P.; Spilling, C. D.; Dupureur, C. M. *Biorg. Med Chem.* 2015, in press http://dx.doi.org/10.1016/j.bmc.2015.01.028.

What is claimed is:

1. A compound comprising a cyclic enolphosphonate or a cyclic enolphosphate, having the structure:

[Chemical structure 1]

wherein n is any of 1 to 20: wherein R is alkyl, benzyl, or aryl; wherein R' is any of C1 to C20:
wherein X is O or $CH_2$; and wherein Y is a fluorescent label; or

[Chemical structure 2]

wherein n is any of 1 to 20; wherein R is alkyl, benzyl, or aryl; wherein R' is any of C1 to C20;
wherein X is O or $CH_2$; and wherein Y is a fluorescent label.

2. The compound of claim 1, having the structure;

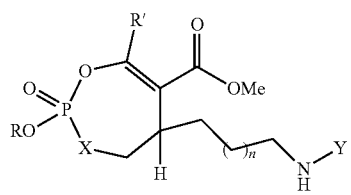

wherein n is any of 1 to 20; wherein R is alkyl, benzyl, or aryl; wherein R' is any of C1 to C20;

wherein X is O or CH$_2$; and wherein Y is a fluorescent label.

3. The compound of claim 1, having the structure;

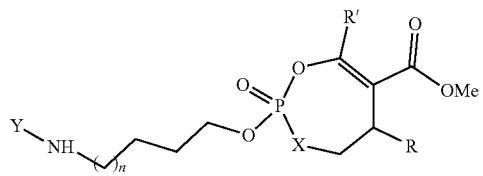

wherein n is any of 1 to 20; wherein R is alkyl, benzyl, or aryl; wherein R' is any of C1 to C20;

wherein X is O or CH$_2$; and wherein Y is a fluorescent label.

4. The compound of claim 2, wherein R' is a methyl group.

5. The compound of claim 2, wherein the fluorescent label is nitrobenzo-2-oxa-1,3-diazole (NBD) or a dansyl group.

6. The compound of claim 1, having the structure;

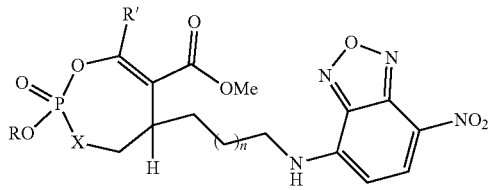

wherein n is any of 1 to 20; wherein R is alkyl, benzyl, or aryl; wherein R' is any one of C1 to C20; and wherein X is O or CH$_2$; or

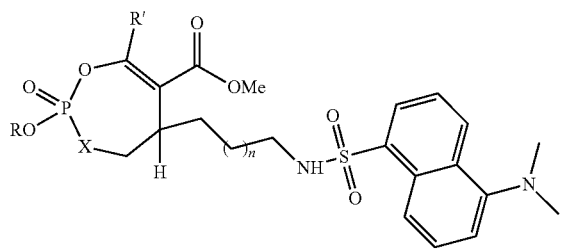

wherein n is any of 1 to 20; wherein R is alkyl, benzyl, or aryl; R' is any one of C1 to C20; and wherein X is O or CH$_2$.

7. The compound of claim 1, having the structure;

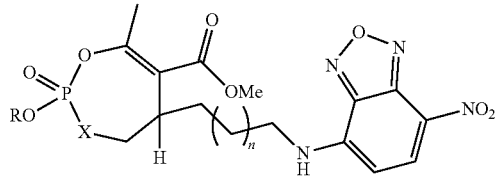

wherein n is any of 1 to 20; wherein R is alkyl, benzyl, or aryl; and wherein X is O or CH$_2$; or

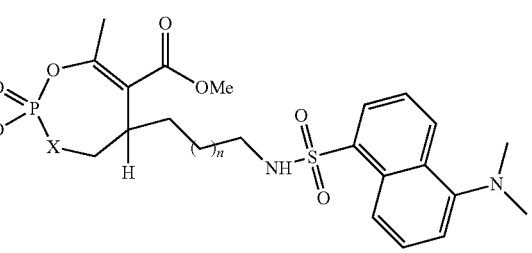

wherein n is any of 1 to 20; wherein R is alkyl, benzyl, or aryl; and wherein X is O or CH$_2$.

8. The compound of claim 1 having the structure;

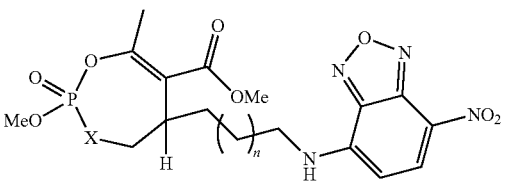

wherein n is any of 1 to 20 and wherein X is O or CH$_2$; or

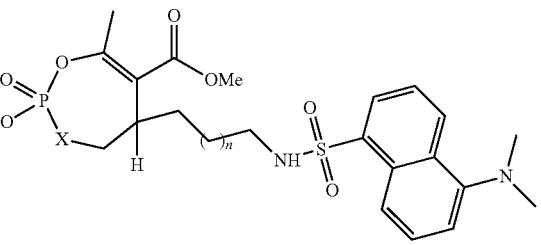

wherein n is any of 1 to 20 and wherein X is O or CH$_2$.

9. The compound of claim 1 having the structure;

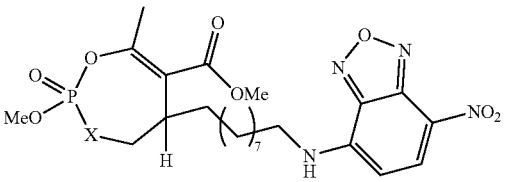

wherein X is O or CH₂; or

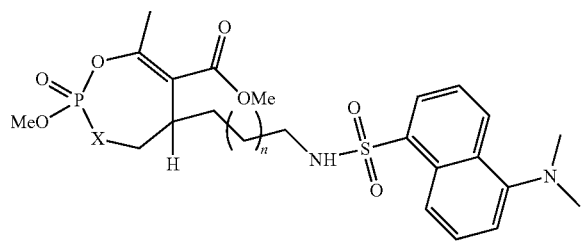

wherein X is O or CH₂.

10. The compound of claim 1, having the structure;

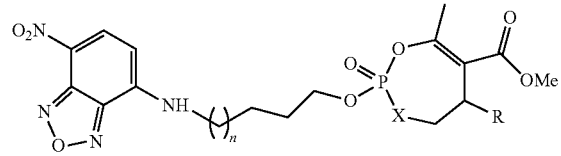

wherein n is any of 1 to 20 and wherein X is O or CH₂; or

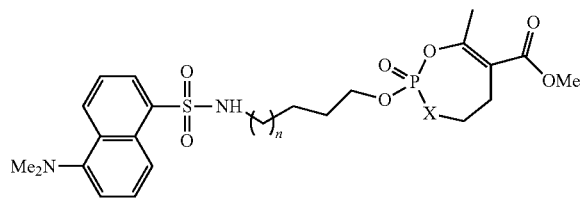

wherein n is any of 1 to 20 and wherein X is O or CH₂.

11. The compound of claim 1, having the structure;

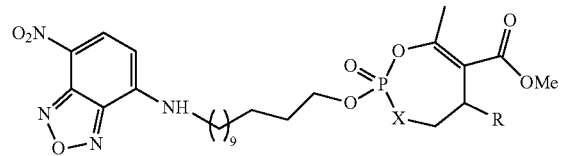

wherein X is O or CH₂; or

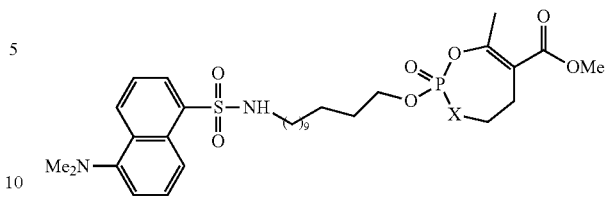

wherein X is O or CH₂.

12. The compound of claim 1, having the structure;

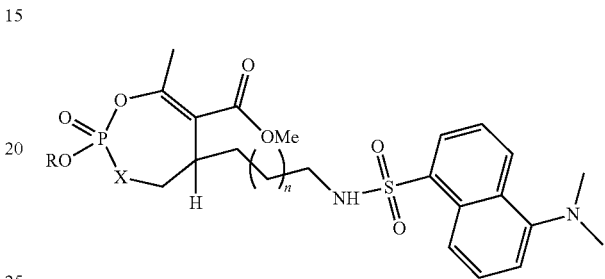

wherein n is any of 1 to 20 and wherein X is O or CH₂.

13. The compound of claim 12, wherein n is 7.

14. The compound of claim 1, wherein the compound inhibits a lipase.

15. The compound of claim 14, wherein said compound covalently binds to an active site serine residue of the lipase.

16. A method of inhibiting an enzyme, the method comprising contacting the enzyme with a compound of claim 1, wherein the enzyme comprises an active site serine residue.

17. The method of claim 16, wherein said enzyme is a lipase.

18. A method of detecting an enzyme, the method comprising contacting the enzyme with a compound of claim 1 to covalently link the compound to the enzyme, wherein the enzyme comprises an active site serine residue, and visualizing the fluorescent label of the compound.

19. The compound of claim 3, wherein R' is a methyl group.

20. The compound of claim 3, wherein the fluorescent label is nitrobenzo-2-oxa-1,3-diazole (NBD) or a dansyl group.

* * * * *